(12) United States Patent
Weinschenk

(10) Patent No.: US 10,493,636 B1
(45) Date of Patent: Dec. 3, 2019

(54) AUTOMATED SYSTEM AND METHOD FOR LUMBER PICKING

(71) Applicant: Steven R. Weinschenk, Rochester, MN (US)

(72) Inventor: Steven R. Weinschenk, Rochester, MN (US)

(73) Assignee: Wein Holding LLC, Rochester, MN (US)

( * ) Notice: Subject to any disclaimer, the term of this patent is extended or adjusted under 35 U.S.C. 154(b) by 2 days.

(21) Appl. No.: 15/426,966

(22) Filed: Feb. 7, 2017

Related U.S. Application Data

(60) Provisional application No. 62/495,830, filed on Sep. 26, 2016.

(51) Int. Cl.
*B25J 15/06* (2006.01)
*B65G 47/91* (2006.01)
*G01N 21/898* (2006.01)

(52) U.S. Cl.
CPC ........ *B25J 15/0633* (2013.01); *B65G 47/912* (2013.01); *B65G 47/917* (2013.01); *G01N 21/8986* (2013.01)

(58) Field of Classification Search
CPC .............. B25J 15/0616; B25J 15/0675; B25J 15/0633; B66C 1/0237; B66C 1/0268
USPC ................................................. 294/186, 188
See application file for complete search history.

(56) References Cited

U.S. PATENT DOCUMENTS

| | | |
|---|---|---|
| 1,804,764 A | 5/1931 | Grant |
| 1,916,567 A | 7/1933 | Grant |
| 2,510,471 A | 6/1950 | Horstkotte |
| 2,806,492 A | 9/1957 | Becker |
| 3,124,181 A | 3/1964 | Clemans |
| 3,815,738 A | 6/1974 | Sweet et al. |

(Continued)

FOREIGN PATENT DOCUMENTS

CN          202899636 U      4/2013

OTHER PUBLICATIONS

Weinmann Holzbausystemtechnik GmbH, "WHP 100 Robotic Material Handling Portal", "Structural Building Components Magazine, downloaded from: http://www.sbcmag.info/sites/default/files/Archive/2008/sep/0809_cc.pdf", Sep./Oct. 2008.

(Continued)

*Primary Examiner* — Ronald P Jarrett
(74) *Attorney, Agent, or Firm* — Charles A. Lemaire; Jonathan M. Rixen; Lemaire Patent Law Firm, P.L.L.C.

(57) ABSTRACT

A system including a lumber-pickup arm having a plurality of suction cups in a staggered configuration to pick up a piece of lumber that may be cracked, crooked or askew on the pile of lumber from which it is to be picked. In some embodiments, the system performs a method that includes locating a selected piece of lumber to be picked up; lowering the pickup arm so that at least some of the plurality of suction cups are seated on a first surface of the selected piece of lumber; reducing air pressure within the at least some of the plurality of suction cups; raising and moving the pickup arm to move the piece of lumber to a first destination; and increasing air pressure within the at least some of the plurality of suction cups to release the piece of lumber at the first destination Cups not holding vacuum are deactivated.

17 Claims, 14 Drawing Sheets

(56) References Cited

U.S. PATENT DOCUMENTS

| | | | |
|---|---|---|---|
| 3,902,605 A * | 9/1975 | Hamilton | B66C 1/0212 |
| | | | 294/64.2 |
| 4,139,035 A | 2/1979 | Bystedt et al. | |
| 4,196,648 A | 4/1980 | Jones et al. | |
| 4,867,213 A | 9/1989 | Bolton et al. | |
| 4,909,112 A | 3/1990 | Rosenthal | |
| 4,951,215 A | 8/1990 | Scherer | |
| 4,992,949 A | 2/1991 | Arden | |
| 5,335,790 A | 8/1994 | Geiger et al. | |
| 5,564,573 A | 10/1996 | Palm et al. | |
| 5,722,646 A * | 3/1998 | Soderberg | B25B 11/005 |
| | | | 269/20 |
| 6,170,163 B1 | 1/2001 | Bordignon et al. | |
| 6,358,352 B1 | 3/2002 | Schmidt | |
| 6,923,614 B2 | 8/2005 | Aylsworth | |
| 7,463,368 B2 | 12/2008 | Morden et al. | |
| 7,621,053 B2 | 11/2009 | Bianchin | |
| 7,801,637 B2 | 9/2010 | Sander | |
| 7,950,316 B2 | 5/2011 | Koskovich | |
| 8,010,216 B2 | 8/2011 | Roise | |
| 8,079,579 B2 | 12/2011 | Fredrickson et al. | |
| 8,782,878 B2 | 7/2014 | Morden et al. | |
| 8,919,001 B2 | 12/2014 | Le Mer et al. | |
| 8,960,244 B1 * | 2/2015 | Aylsworth | B27B 31/00 |
| | | | 144/245.5 |
| 9,316,506 B2 | 4/2016 | Aspen | |
| 9,369,632 B2 | 6/2016 | Short | |
| 10,080,003 B2 | 9/2018 | Tone | |
| 2005/0013472 A1 | 1/2005 | Gauthier | |
| 2005/0027389 A1 | 2/2005 | Hadaway et al. | |
| 2006/0180432 A1 * | 8/2006 | Kyrstein | B65G 47/252 |
| | | | 198/379 |
| 2007/0220825 A1 | 9/2007 | Davis | |
| 2008/0140248 A1 | 6/2008 | Moore | |
| 2008/0184856 A1 | 8/2008 | Koskovich | |
| 2008/0223768 A1 | 9/2008 | Ahrens | |
| 2008/0243270 A1 | 10/2008 | Jones | |
| 2008/0283151 A1 | 11/2008 | Floyd | |
| 2008/0297740 A1 | 12/2008 | Huynh et al. | |
| 2010/0201702 A1 | 8/2010 | Franik et al. | |
| 2013/0129464 A1 * | 5/2013 | Regan | B25J 15/0691 |
| | | | 414/800 |
| 2014/0138290 A1 | 5/2014 | Saastamo | |
| 2014/0238546 A1 | 8/2014 | Barker | |
| 2014/0290456 A1 | 10/2014 | Brooks | |
| 2014/0341444 A1 | 11/2014 | Hou et al. | |
| 2015/0054792 A1 | 2/2015 | Kuki | |
| 2016/0103115 A1 | 4/2016 | Hamby | |
| 2016/0153917 A1 | 6/2016 | Couturier | |
| 2017/0050334 A1 | 2/2017 | Aylsworth | |
| 2017/0057113 A1 | 3/2017 | Aylsworth | |
| 2017/0217022 A1 | 8/2017 | Aylsworth | |
| 2017/0274489 A1 | 9/2017 | Baratta | |
| 2017/0305029 A1 | 10/2017 | Aylsworth | |
| 2017/0355083 A1 * | 12/2017 | Wigren | B25J 15/0633 |
| 2018/0001508 A1 | 1/2018 | Aylsworth | |

OTHER PUBLICATIONS

Weinmann Holzbausystemtechnik GmbH, "Carpentry machines WBS and WBZ", "Downloaded from internet: http://www.homag.com/fileadmin/product/houseconstruction/brochures/weinmann-carpentry-machines-WBS-and-WBZ-english.pdf", May 2016, Publisher: Publication at least as early May 2016.

Acer Inc., "Wood Runner (manual)", "Internet address: https://www.mitek-us.com/uploadedFiles/_RedesignSite/Content/documents/troubleshooting/blade-software/Blade-WoodRunner-Manual.pdf", Mar. 2, 2014.

"Vacuum Lifter (Youtube video)", "Video may be viewed at internet address: https://www.youtube.com/watch?v=PETPO3deHdg", 2011, Publisher: in related U.S. Appl. No. 15/408,374.

"Matchpoint Blade with 16 bay wood runner (Youtube video)", "Video may be viewed at internet address: https://www.youtube.com/watch?v=r_kTAMKVQIw", 2015, Publisher: in related U.S. Appl. No. 15/408,374.

* cited by examiner

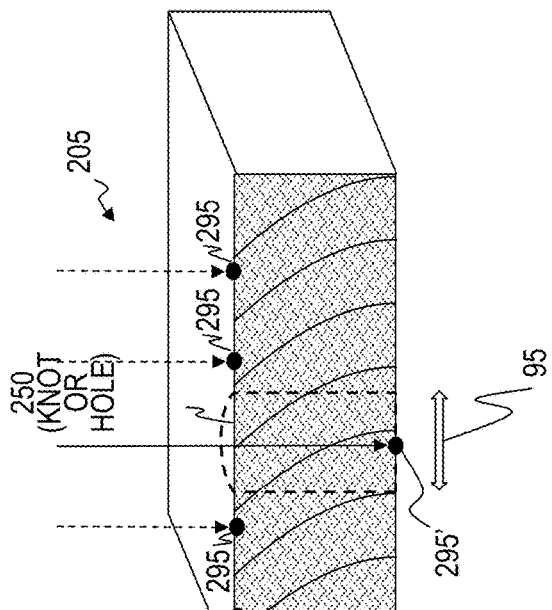
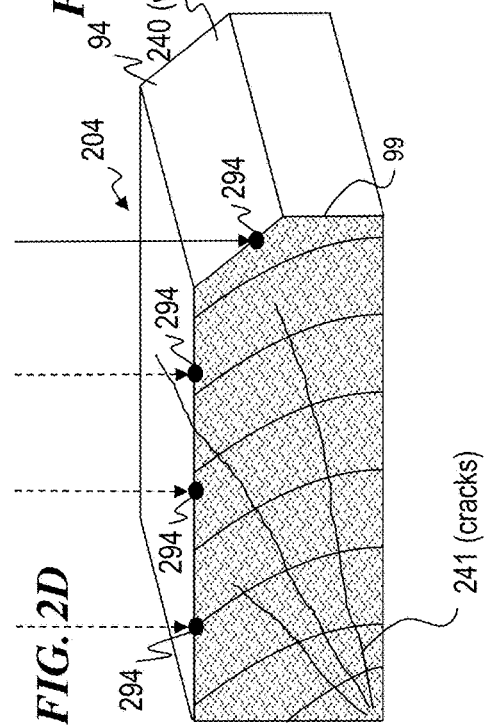
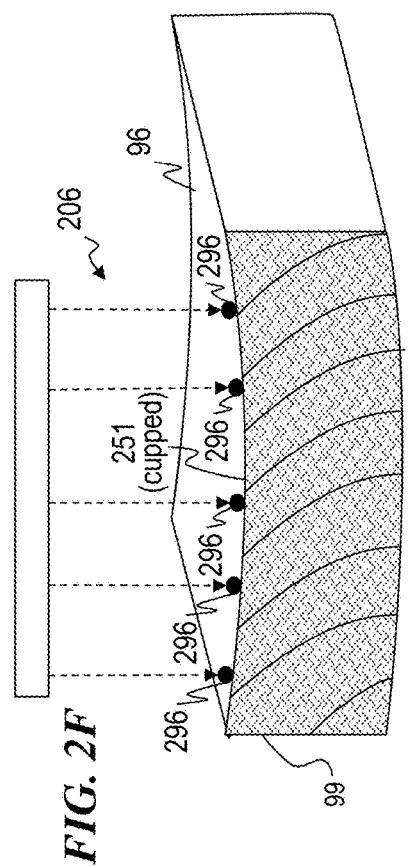
FIG. 2D
FIG. 2E
FIG. 2F

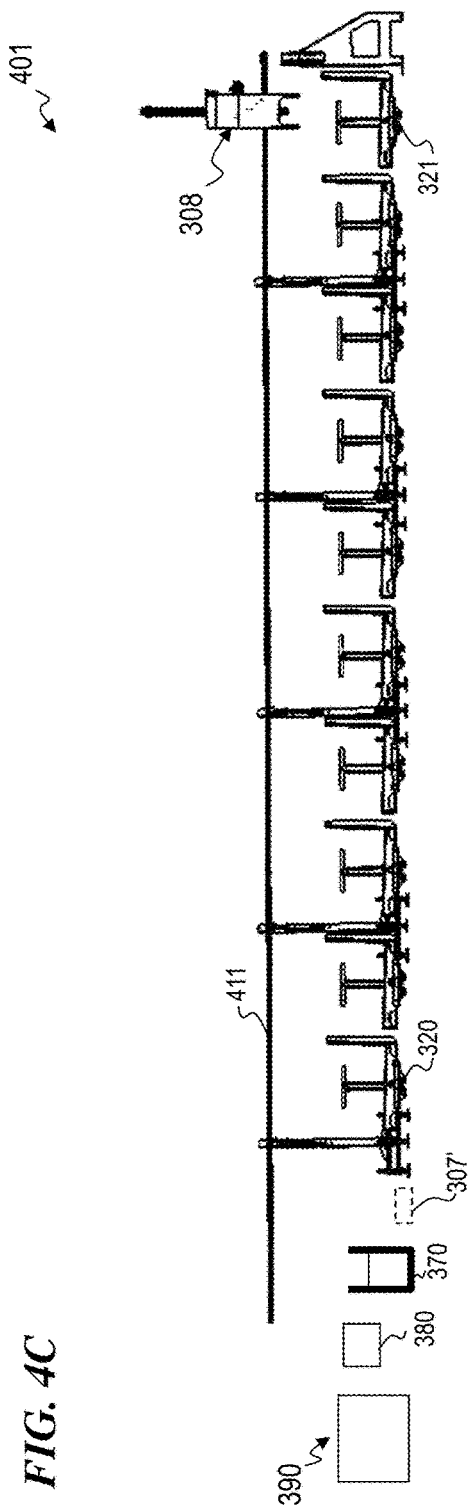
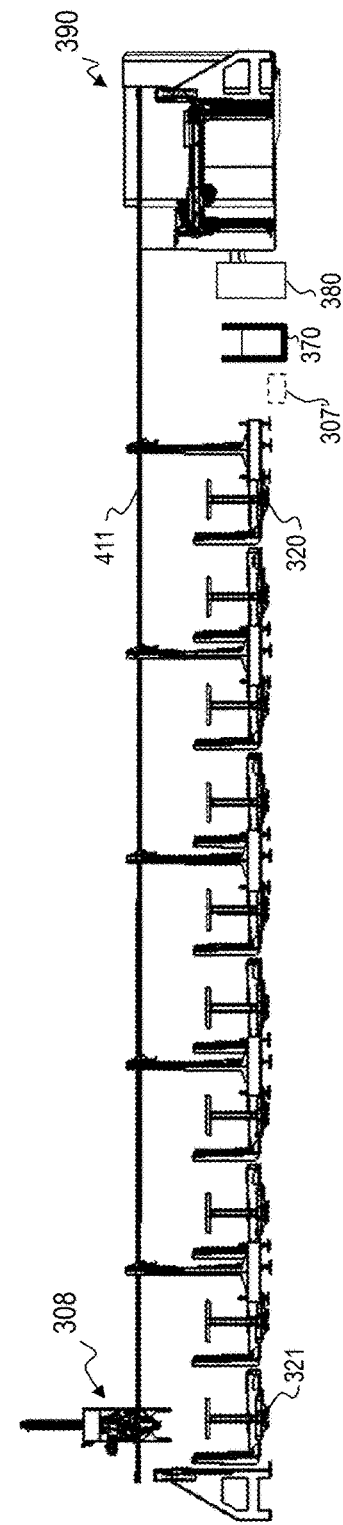
FIG. 4C
FIG. 4D

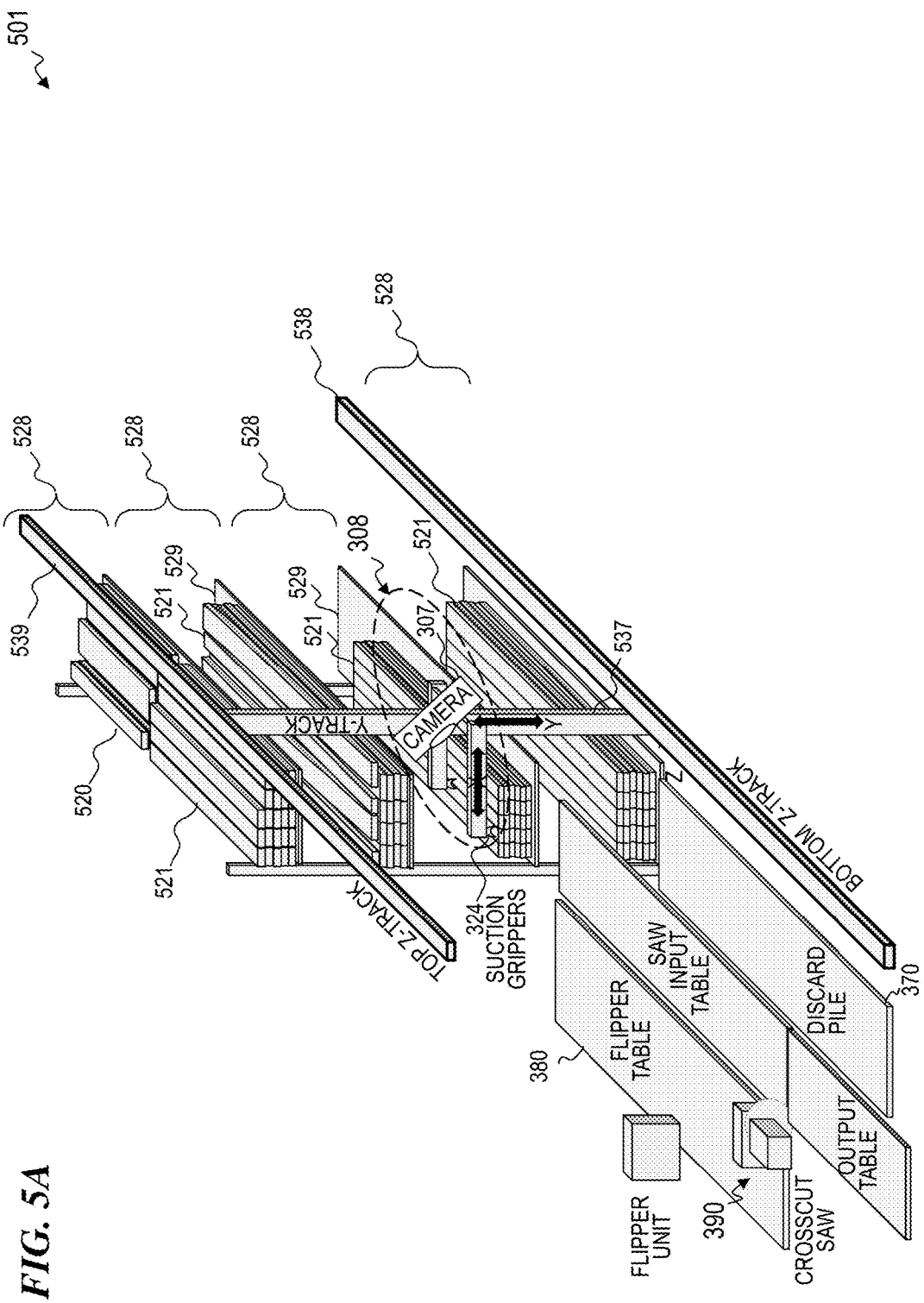

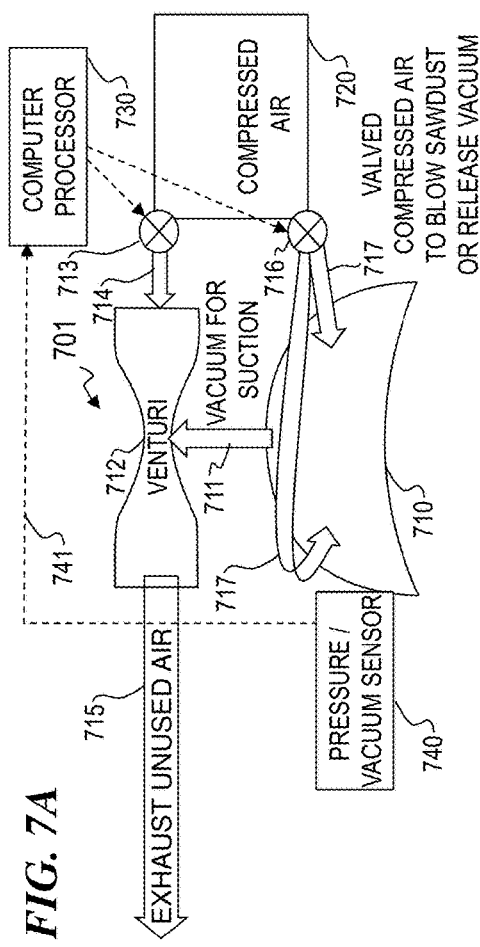
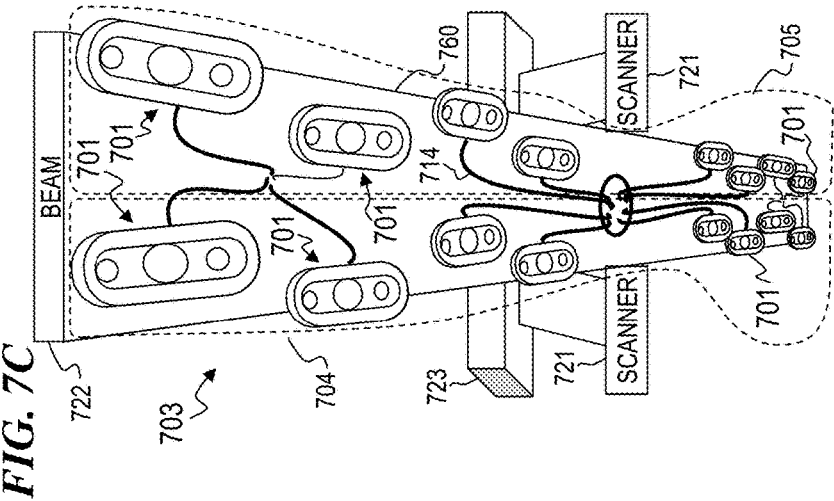
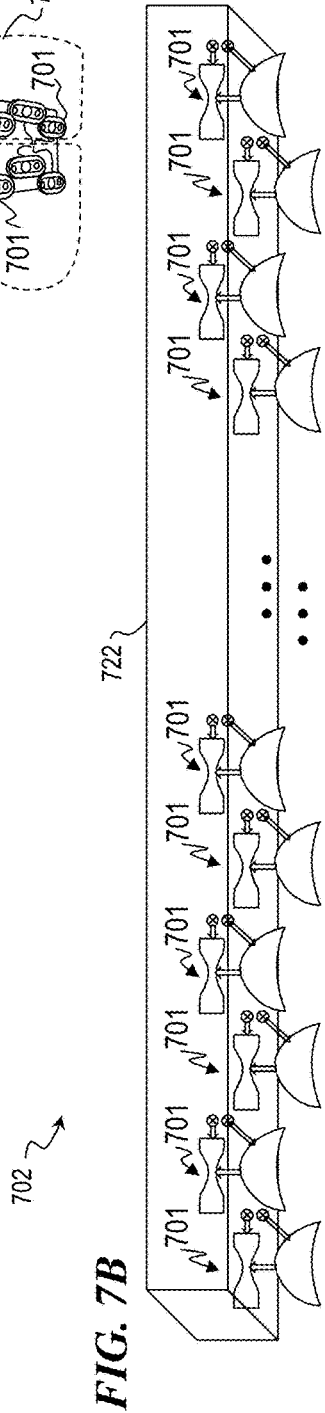

AUTOMATED SYSTEM AND METHOD FOR LUMBER PICKING

CROSS-REFERENCE TO RELATED APPLICATION

This application claims priority benefit, under 35 U.S.C. § 119(e), of U.S. Provisional Patent Application 62/495,830, filed Sep. 26, 2016 by Steven Weinschenk, titled "MULTI-HEADED LINEAR SAW," which is incorporated herein by reference in its entirety. This invention is related to:

U.S. Provisional Patent Application 62/388,048, filed Jan. 14, 2016 by Steven Weinschenk, titled "AUTOMATED SYSTEM AND METHOD TO ENHANCE SAFETY AND STRENGTH OF WOOD TRUSS STRUCTURES,"

U.S. patent application Ser. No. 15/408,369, filed Jan. 17, 2017 by Steven Weinschenk, titled "AUTOMATED SYSTEM AND METHOD TO ENHANCE SAFETY AND STRENGTH OF WOOD TRUSS STRUCTURES" (which issued as U.S. Pat. No. 10,239,225 on Mar. 26, 2019), U.S. patent application Ser. No. 15/408,374, filed Jan. 17, 2017 by Steven Weinschenk, titled "AUTOMATED SYSTEM AND METHOD FOR LUMBER ANALYSIS,"

U.S. Provisional Patent Application 62/144,859 filed Apr. 8, 2015 by Steven Weinschenk, titled "DIGITAL PROJECTION SYSTEM AND METHOD FOR WORKPIECE ASSEMBLY," and U.S. patent application Ser. No. 15/093,732 filed Apr. 7, 2016 by Steven R. Weinschenk et al., titled "DIGITAL PROJECTION SYSTEM AND METHOD FOR WORKPIECE ASSEMBLY" (which issued as U.S. Pat. No. 10,210,607 on Feb. 19, 2019);

which are each incorporated herein by reference in their entirety.

FIELD OF THE INVENTION

The present invention relates to devices and methods to workpiece assembly, and in particular to automated systems and methods for lumber picking that use suction "cups" that are staggered rather than being aligned along a straight line. Some embodiments organize each incoming stack of lumber in one of a plurality of vertically spaced apart bunks, one on top of another, and provide a gantry that picks a selected board from the stack of lumber on a selected bunk, and moves the board in a direction generally parallel to the long axis of the board from the bunk to one of a plurality of processing stations, wherein the plurality of processing stations includes a flipping station and/or a sawing station.

BACKGROUND OF THE INVENTION

One problem with today's conventional technology is that, when manually loading wood into the infeed systems, the human operator needs to determine how to orient the wood, which increases the cost of labor when manufacturing structures using wood boards (lumber). As used herein, "crook" is a lumber feature or defect where the widest faces of the piece of lumber are substantially planar but there is a curvature along the length of the narrower faces of the piece of lumber. The "crown" is the convex one of the narrower faces of the piece of lumber with a crook. The crown should be orientated to optimize with the wood saw equipment. Certain wood trusses and pre-assembled walls are more secure if the crown of the wood is oriented correctly (both when the board is loaded into a sawing station, and when the cut board is assembled into a truss, a pre-assembled wall, or the like). Conventional automated or partially automated systems are unable to determine and/or distinguish the crown of the lumber.

U.S. Pat. No. 6,170,163 to Robert A. Bordignon et al. titled "METHOD OF ASSEMBLING COMPONENTS OF AN ASSEMBLY USING A LASER IMAGE SYSTEM," issued Jan. 9, 2001, and is incorporated herein by reference. In U.S. Pat. No. 6,170,163 Bordignon et al. describe a method of assembling components of an assembly, such as the components of a truss, using a laser imaging system in combination with assembly jigs. The jigs may be slideably mounted on an assembly table wherein the jigs include laser alignment indicia on a top surface of the jigs spaced a predetermined distance from a side surface of the jigs. The method includes projecting an enlarged laser generated outline of at least a portion of the components to be assembled which is spaced laterally from an outline or template of the components in the assembled position a distance equal to the distance between the laser alignment indicia and the side surface of the jigs and spaced vertically a distance equal to the distance between the indicia and the work surface. The jigs are then moved on the work surface to align the laser alignment indicia with the enlarged outline and affixed relative to the work surface. Finally, the components are assembled on the work surface in generally abutting relation with the side surfaces of the jigs and assembled. Where the assembly method of this invention is used for assembling trusses, the laser generated outline may be used to orient the truss planks.

U.S. Pat. No. 7,463,368 to Morden et al. titled "LASER PROJECTION SYSTEM, INTELLIGENT DATA CORRECTION SYSTEM AND METHOD," issued Dec. 9, 2008, and is incorporated herein by reference. In U.S. Pat. No. 7,463,368 Morden et al. describe a laser projection system, intelligent data correction system and method which corrects for differences between the as-built condition and the as-designed condition of a workpiece which includes determining the as-built condition of a workpiece with a digitizer scanner and modifying data of the as-built condition or the data of a laser projection based upon the data received from the digitizer scanner of the as-built condition. A preferred intelligent data correction system includes metrology receivers fixed relative to the digitizer scanner and the workpiece and a metrology transmitter to determine the precise location and orientation of the digitizer scanner relative to the workpiece.

U.S. Pat. No. 7,621,053 to Edward S. Bianchin titled "ASSEMBLY APPARATUS," issued Nov. 24, 2009, and is incorporated herein by reference. In U.S. Pat. No. 7,621,053 Bianchin describes an assembly apparatus for assembling components including a work surface, a laser projector, a computer controlling the laser projector to protect a laser image on the work surface, and an ejector lifting a completed assembly from the work surface having a retro-reflective surface within a field of view of the laser projector when the ejector is lifted, such that the laser projector scans the retro-reflective surface and the computer determines at least one of the number of completed assemblies made and the time required to make the assembly.

United States Patent Publication 2010/0201702 of Franik et al. published Aug. 12, 2010 with the title "DIGITAL IMAGE PROJECTION LUMINAIRE SYSTEMS," and is incorporated herein by reference. In Patent Publication 2010/0201702 Franik et al. describe improvements to digital imagine projection systems and for seamless blending of images projected from a plurality of digital image projectors to create combined images from multiple projectors where the user is provided with independent control of the blend area and of independent control of image parameters within said variable blend area such as brightness, contrast, individual color intensity and gamma correction.

U.S. Pat. No. 8,079,579 to Fredrickson et al. titled "Automatic truss jig setting system," issued Dec. 20, 2011, and is incorporated herein by reference. In U.S. Pat. No. 8,079,579 Fredrickson et al. describe an automatic truss jig setting system that includes a table including a plurality of segments with a side edge of adjacent segments defining a slot. At least one pin assembly, and optionally a pair of pin assemblies, is movable independently of each other along the slot. Movement apparatus is provided for independently moving the pin assemblies along the slot. Each of the side edges of the segments associated with the slot defines a substantially vertical plane with a zone being defined between the substantially vertical planes of the side edges, and the movement apparatus is located substantially outside of the zone of the slot. The invention may optionally include a system for handling the obstruction of pin assembly movement, and a system for keeping track of the position of the pin assembly when the pin assembly has encountered an obstruction.

U.S. Pat. No. 8,782,878 to Morden et al., titled "FASTENER AUTOMATION SYSTEM," issued Jul. 22, 2014, and is incorporated herein by reference. In U.S. Pat. No. 8,782,878, Morden et al. describe a fastener automation system for assembly of fasteners to a substrate, which includes a projection system for projecting an image on a substrate of a predetermined location of a correct fastener to be installed in the substrate and data relating to the correct fastener and the substrate, and a computer operably associated with the projection system storing data regarding the correct fastener and the predetermined location on the substrate where the correct fastener is to be installed. An automated method of installing a fastener in a substrate at a predetermined location includes using a projector system to identify a predetermined location for installation of a correct fastener to the substrate, collecting data regarding the correct fastener installation at the predetermined location and storing the data in a computer, and installing the correct fastener in the substrate at the predetermined location based upon the data.

United States Patent Publication 2008/0297740 of Huynh et al. published Dec. 4, 2008 with the title "Projection system and method of use thereof," and is incorporated herein by reference. In Patent Publication 2008/0297740 Huynh et al. describe a projection system and method of use thereof, wherein a computer in electrical communication with at least one projector projects a layout, preferably onto a floor projection surface utilizing short throw lenses, wherein the layout preferably comprises a grid and indicia relating to an exhibitor.

U.S. Pat. No. 8,919,001 to Le Mer et al. titled "METHOD AND SYSTEM FOR HELPING TO POSITION A COMPONENT ON A STRUCTURAL ELEMENT," issued Dec. 30, 2014, and is incorporated herein by reference. In U.S. Pat. No. 8,919,001 Le Mer et al. describe a method for helping to position a component on the wall of a structural element, including the steps: elaborating an image to be projected on the wall, from a virtual model of the structure and from the positioning of a projector with respect to the structure, and an additional motif providing positioning information of the piece with respect to the direction normal to the wall, projecting the image on the structural element by means of the projector; placing the base of the piece inside an outline of the image projected on the wall; and, while keeping contact between the piece and the structural element, modifying the positioning of the piece with respect to the direction normal to the wall, until the predefined set of points of the piece coincides with the motif.

U.S. Pat. No. 8,960,244 to Aylsworth et al. titled "AUTOMATED LUMBER RETRIEVAL AND DELIVERY," issued Feb. 24, 2015, and is incorporated herein by reference. In U.S. Pat. No. 8,960,244 Aylsworth et al. describe an automated lumber handling system that laser-scans the top profile of multiple stacks of lumber, each of which contain boards of a unique size. Based on the scanned profiles, the system determines the order in which individual boards from a chosen stack should be transferred to a numerically controlled saw. The saw cuts the boards to proper size, and in the proper sequence to facilitate orderly assembly of a roof truss or prefabricated wall. In some examples, the system lifts individual boards by driving two retractable screws, or some other piercing tool, down into the upward facing surface of the board. A track mounted cantilever, holding the screws and a laser unit, translates over the lumber stacks to retrieve and deliver individual boards and, while doing so, the laser repeatedly scans the stacked lumber profiles on-the-fly to continuously update the profiles. The open cantilever design facilitates replenishing the stacks of lumber.

Chinese Patent Publication CN 202899636 U published Apr. 24, 2013 with the title "Discrete assembly device for large-span rectangular spatially warped tube truss," and is incorporated herein by reference. This Chinese Patent Publication CN 202899636 describes a discrete assembly device for a large-span rectangular spatially warped tube truss. The device consists of a base, two supporting tubes fixedly connected to the two sides of the base, and tube brackets fixedly connected to the tops of the supporting tubes, wherein grooves of which the diameter is matched with that of a lower chord of an assembly section truss are formed on the tube brackets. The on-site assembly difficulty of the large-span rectangular spatially warped truss is reduced, assembly accuracy and speed are greatly improved, and construction materials are saved.

There is a need in the art for better pickers and grabbers for temporarily attaching a piece of lumber to a moving arm in automated systems and methods for lumber analysis, sorting, adjustment, and sawing for workpiece assembly, such as the assembly of wooden roof trusses, pre-assembled walls, and the like.

SUMMARY OF THE INVENTION

In some embodiments, the present invention provides a vacuum-activated picker arm that includes a plurality of suction cups that are optionally staggered at one or more distances on either side of a straight line, in order that if one or more of the suction cups fails to achieve a satisfactory grip on a piece of lumber (perhaps due to a crack or other defect in the piece of lumber, others of the plurality of suction cups will achieve enough of a grip to reliably pick up and move the piece of lumber. Some embodiments further include a plurality of compressed-air blowers to remove sawdust or other debris that may be on the piece of lumber, in order to reduce the amount of leakage at the plurality of suction cups. Some embodiments further include a plurality of compressed-air blowers to speed the release of the piece of lumber once it reaches its destination.

In some embodiments, the present invention provides a method and associated system that includes a computer processor, wherein the computer processor includes: a plurality of input data devices, a plurality of output data devices, and a plurality of sensors, and wherein the system further includes a mechanical assembly integrated with the computer processor to analyze the geometry of a piece of wood or lumber and, if necessary, reposition the piece and convey the piece to a saw or to a reject station, based on software code executing in the computer processor. Some embodiments organize each incoming stack of lumber in one of a plurality of vertically spaced apart bunks, one on top of another, and provide a gantry that picks a selected board from the stack of lumber on a selected bunk, and moves to board in a direction generally parallel to the long axis of the board from the bunk to one of a plurality of processing stations, wherein the plurality of processing stations includes a flipping station and/or a sawing station. Organizing the lumber bunks in vertical assemblies greatly reduces the footprint of the overall system, thus making more efficient use of valuable factory space and reducing costs. Using the present invention, one can buy lower-grade lumber and sort the boards to obtain suitable and usable pieces for a given end product, thus reducing cost and improving quality of the end product.

In some embodiments, the present invention provides a system and associated method that operates on a computer processor having a plurality of input data devices, a plurality of output data devices, a plurality of sensors, a database, software code, and a wireless interface, wherein the computer processor is integrated with mechanical components, and wherein the method includes eliciting and receiving into the computer processor data parameters from a first human user; obtaining incoming data points about lumber from the plurality of sensors (e.g., in some embodiments, from optical point distance sensors and/or three-dimensional (3D) machine-vision systems); processing the data parameters to obtain processed data parameters; storing the processed data parameters; comparing the incoming data points from the plurality of sensors to the stored data parameters to obtain comparison results; and, based on the comparison results, (1) directing the mechanical components to reject the wood to a preprogrammed position, (2) directing the mechanical components to feed the lumber into a saw assembly as positioned, or (3) directing the mechanical components to reposition the lumber to a more optimal position prior to feeding the lumber to a saw assembly.

BRIEF DESCRIPTION OF THE FIGURES

FIG. 2D is a schematic diagram 204 showing exemplary data points used to detect wane 240 and cracks 241 in a piece of lumber 99, according to some embodiments of the present invention.

FIG. 2E is a schematic diagram 205 showing exemplary data points used to detect a knot 250 in a piece of lumber 99, according to some embodiments of the present invention.

FIG. 2F is a schematic diagram 206 showing exemplary data points used to detect cupping 251 in a piece of lumber 99, according to some embodiments of the present invention.

FIG. 4C is a front-end view of lumber-analyzer system 401, according to some embodiments of the present invention.

FIG. 4D is a back-end view of lumber-analyzer system 401, according to some embodiments of the present invention.

FIG. 5A is a schematic diagram of a lumber-analyzer system 501, according to some embodiments of the present invention.

FIG. 7A is a schematic block diagram of a vacuum-activated lumber picker suction-cup assembly 701, according to some embodiments of the present invention.

FIG. 7B is a schematic side-view block diagram of a vacuum-activated lumber picker assembly 702 that includes a plurality of suction-cup assemblies 701, according to some embodiments of the present invention.

FIG. 7C is a perspective view of a vacuum-activated lumber picker assembly 703 that includes a plurality of suction-cup assemblies 701, according to some embodiments of the present invention.

COPYRIGHT NOTICE/PERMISSION

Figure 1:
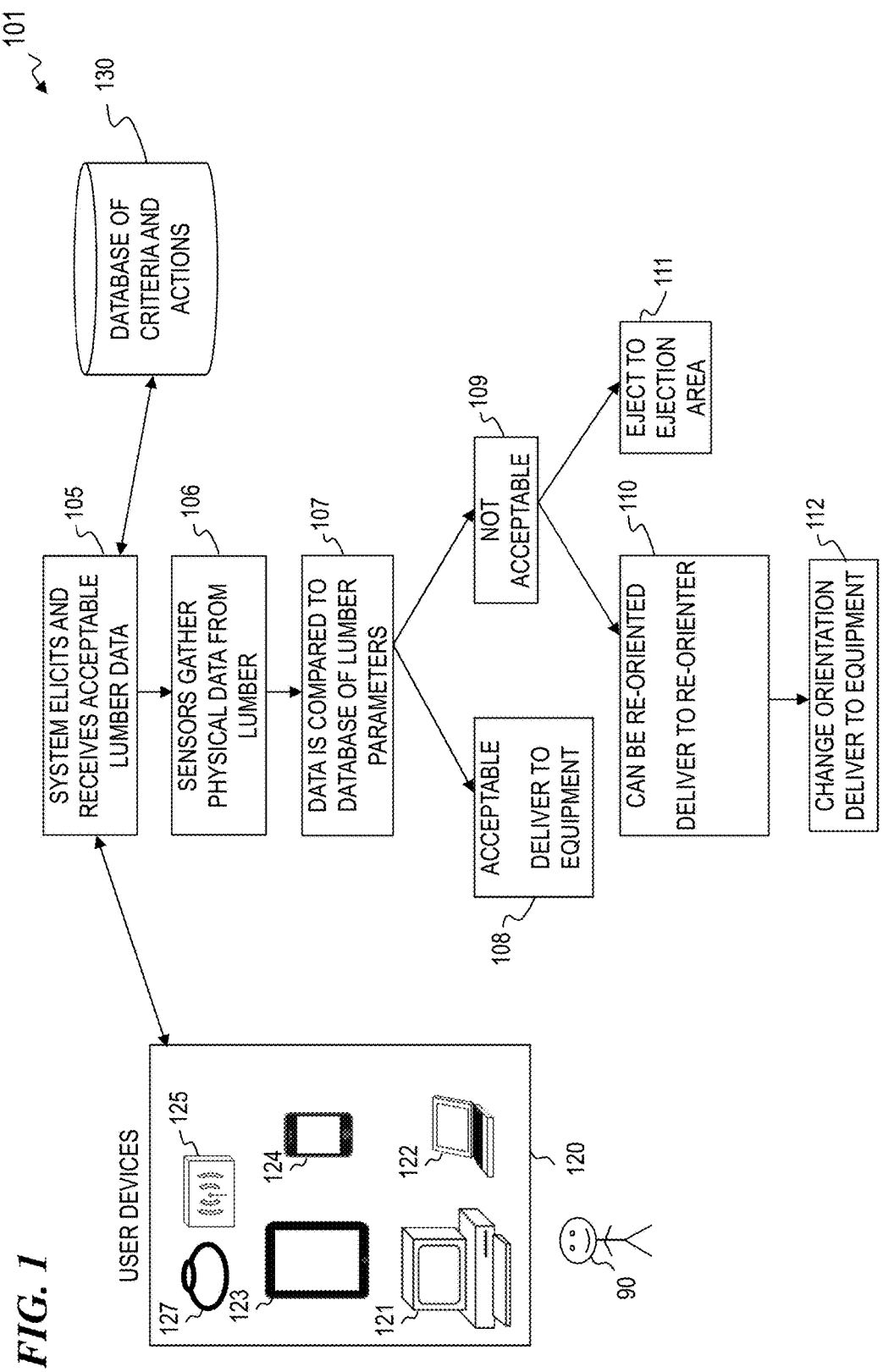
FIG. 1 is a flowchart 101 of one embodiment of the system data processing and software integration of the present invention.

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described herein and in the drawings hereto in the attached appendices: Copyright © 2014-2017, Steven R. Weinschenk, All Rights Reserved.

DETAILED DESCRIPTION OF THE INVENTION

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter associated with such marks.

As used herein, "crook" is a lumber feature or defect where the widest faces of the piece of lumber are substantially planar but there is a curvature along the length of the narrower faces of the piece of lumber. The "crown" is the convex one of the narrower faces of the piece of lumber with a crook. See FIG. 2A.

As used herein, "bow" is a lumber feature or defect where the narrower faces of the piece of lumber are substantially planar but there is a curvature along the length of the wider faces of the piece of lumber. See FIG. 2B.

As used herein, "twist" is a lumber feature or defect in which there are curvatures across multiple surfaces in the lumber. See FIG. 2C.

As used herein, "wane" is a lumber feature or defect that is characterized by bark or insufficient wood at a corner or along an edge, due to the piece of lumber being cut from an outer edge of the log. See FIG. 2D.

As used herein, "knot" is a lumber feature or defect that is characterized by a separated branch piece or hole in a piece of lumber. See FIG. 2E.

As used herein, "cup" is a lumber feature or defect where there is a curvature the width of the widest face of the lumber, in which the edges are higher or lower than the center of the piece of lumber. See FIG. 2F.

In some embodiments, the present invention provides a crown-detection system for wood truss lumber infeed saw equipment for enhanced structural support and safety features. In some embodiments, the present invention provides an automated "AutoCurvature System" that detects the crown orientation of the lumber. In some embodiments, after detection by the AutoCurvature System that determines the bow, crown, or twist of a piece of lumber, the AutoCurvature System automatically rejects the wood piece, or the wood piece is reoriented.

In some embodiments, the AutoCurvature System elicits information from the environment or a human operator. In some embodiments, upon receipt of the initial data points, the AutoCurvature System sensors detect the curvature of the lumber piece, and compare the parameters from the detection to an acceptable range of data points pre-programmed in the AutoCurvature System (in some such embodiments, the comparison is performed using an algorithm).

In some embodiments, the AutoCurvature System of the present invention determines: (1) that the lumber should be rejected, (2) that the direction of the lumber needs to be changed, or (3) that the lumber should be fed, as situated/oriented, into the saw.

In some embodiments, the sensors of the present invention include a plurality of single-point distance-detecting optical systems. In some embodiments, the sensors also or alternatively include multiple-point optical systems (e.g., in some embodiments, the present invention includes one or more three-dimensional (3D) O3D302 sensors from IFM Efector, Inc., 1100 Atwater Drive, Malvern, Pa. 19355). In some embodiments, the sensors include mechanically driven electrical sensors. In some embodiments, the sensors include monochromatic-camera or color-camera technologies. In some embodiments, the sensors include laser distance detectors. In some embodiments, the sensors include motion detection. In some embodiments, the sensors include temperature detection. In some embodiments, the sensors include weight detection. In some embodiments, the sensors include moisture detection.

FIG. 1 is a flowchart 101 of one embodiment of the system data processing and software integration of the present invention. In some embodiments, at block 105, the system (e.g., system 301 of FIG. 3) elicits acceptable lumber data from a user 90 and/or from a stored set of data 130 that correlates characteristics of lumber with certain actions to be taken by the system, based on the end product to be built using the pieces of lumber. In some embodiments, system 301, using method 101, elicits and receives, from a human user 90 using an input/output device 120, selection data that the system uses to selects one or more sets of criteria and corresponding actions from a stored database that has been pre-loaded with a plurality of sets of criteria and corresponding actions that have been predetermined to meet requirements for each of a plurality of possible end products to be built using the pieces of lumber. In some embodiments, the present invention utilizes one or more of the user devices 120 of each user 90, such as a desktop personal computer 121, laptop computer 122, tablet computer 123, smartphone 124, a position-sensing device 125 (which in some embodiments, is a stand-alone Global Positioning System (GPS) device (such as made by Garmin Ltd.) or in other embodiments, is part of a position-tracking system or another device such as a smartphone 124 or the like), and/or other devices such as wearable computers in clothing or smartwatches 127 or the like. In some embodiments, the human user 90 responds to the eliciting of information by indicating to system 301 which one of a plurality possible end-products is to be manufactured, wherein the criteria and actions for each respective end product is customized and optimized for that respective end product and stored in database 130, such that when an indication is received from the device 120 of user 90, that set of data is then used for the operations of blocks 106 through 112. In some embodiments, at block 106, sensors gather physical data from lumber. In some embodiments, distance data is received from each of one or more sensors for each of a plurality of point locations on one or more pieces of lumber. In some embodiments, those distance data are processed to obtain XYZ coordinates for each of the plurality of point locations, and curve-fitting algorithms are applied to find edges and surfaces of the one or more pieces of lumber, and determine the shapes and curves of edges and surfaces of the lumber. In some embodiments, at block 107, the physical geometric data is compared to the selected set of lumber parameters to obtain data comparison results. In some embodiments, at block 108, the data comparison results have been determined to be acceptable and therefore the piece of lumber is delivered to the processing equipment for the end product being manufactured (such as, for example, an automated saw). In some embodiments, at block 109, the data comparison results have been determined to be unacceptable and un-fixable (at least in regards to this particular station and the uses to which the lumber is to be applied in a commercially reasonable fashion), so control is passed to block 111, and the piece of lumber is delivered to the rejection area. In some embodiments, at block 110, the piece of lumber is determined to be processable if reoriented, so that piece should be reoriented, so as a result the lumber is delivered to a reorienter. In some embodiments, at box 112, the orientation of the lumber is changed by the reorienter and then the now-reoriented piece of lumber is delivered to the processing equipment for the end product being manufactured (such as the automated saw).

Figure 2A:
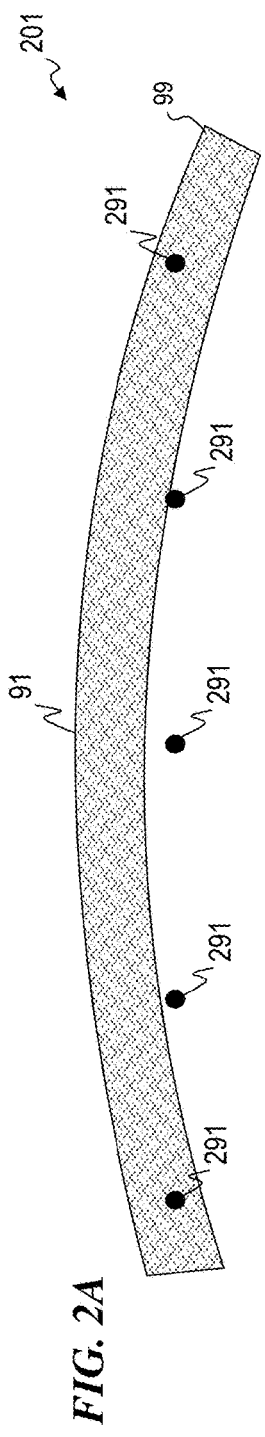
FIG. 2A is a schematic diagram 201 showing exemplary data points used to detect crook in a piece of lumber 99, according to some embodiments of the present invention.

FIG. 2A is a schematic diagram 201 showing a top view of a plurality of exemplary data points 291 gathered along the length of a board and used to detect crook in a piece of lumber 99, and if crook is detected, used to determine the crown face 91 and the amount of curve on the crown face 91, according to some embodiments of the present invention.

Figure 2B:
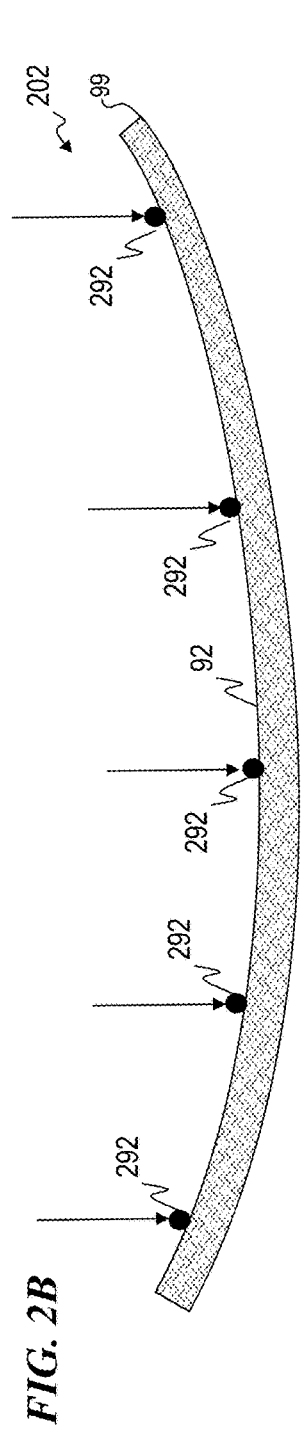
FIG. 2B is a schematic diagram 202 showing exemplary data points used to detect bow in a piece of lumber 99, according to some embodiments of the present invention.

FIG. 2B is a schematic diagram 202 showing a side view of a plurality of exemplary data points 292 gathered along the length of a board and used to detect bow in a piece of lumber 99, and if bow is detected, used to determine the amount and direction of curve on the bowed face 92, according to some embodiments of the present invention.

Figure 2C:
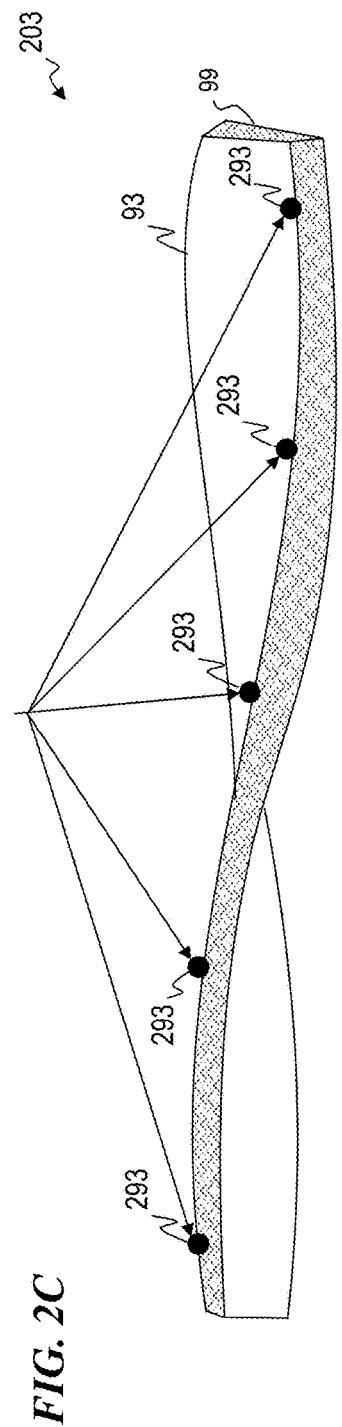
FIG. 2C is a schematic diagram 203 showing exemplary data points used to detect twist in a piece of lumber 99, according to some embodiments of the present invention.

FIG. 2C is a schematic diagram 203 showing a side view of a plurality of exemplary data points 293 gathered along the length of a board and used to detect twist in a piece of lumber 99, and if twist is detected, used to determine the amount and direction of curve on the twisted face 93, according to some embodiments of the present invention.

FIG. 2D is a schematic diagram 204 showing a perspective view of a plurality of exemplary data points 294 gathered across the width of a board and used to detect cracks 241 and wane 240 in a piece of lumber 99, and if cracks and/or wane are detected, used to determine the amount and position of any crack(s) and/or the amount and which corner(s) are missing on the wane surface 94, according to some embodiments of the present invention.

FIG. 2E is a schematic diagram 205 showing a perspective view of a plurality of exemplary data points 295 gathered across the width of a board and used to detect a knot 250 in a piece of lumber 99, and if one or more knots are detected, used to determine the size and position of any knots and/or the amount (size) and positions of the missing wood at the knot position 95, according to some embodiments of the present invention. In some embodiments, one or more of the data points (e.g., point 295') indicates a data point in the middle of a board that is well below the other data points 295 on the top surface.

FIG. 2F is a schematic diagram 206 showing a perspective view of a plurality of exemplary data points 296 gathered across the width of a board and used to detect cupping 251 in a piece of lumber 99, and if cupping is detected, used to determine the amount and direction of curve/cupping on the cupped face 96, according to some embodiments of the present invention.

Figure 3A:
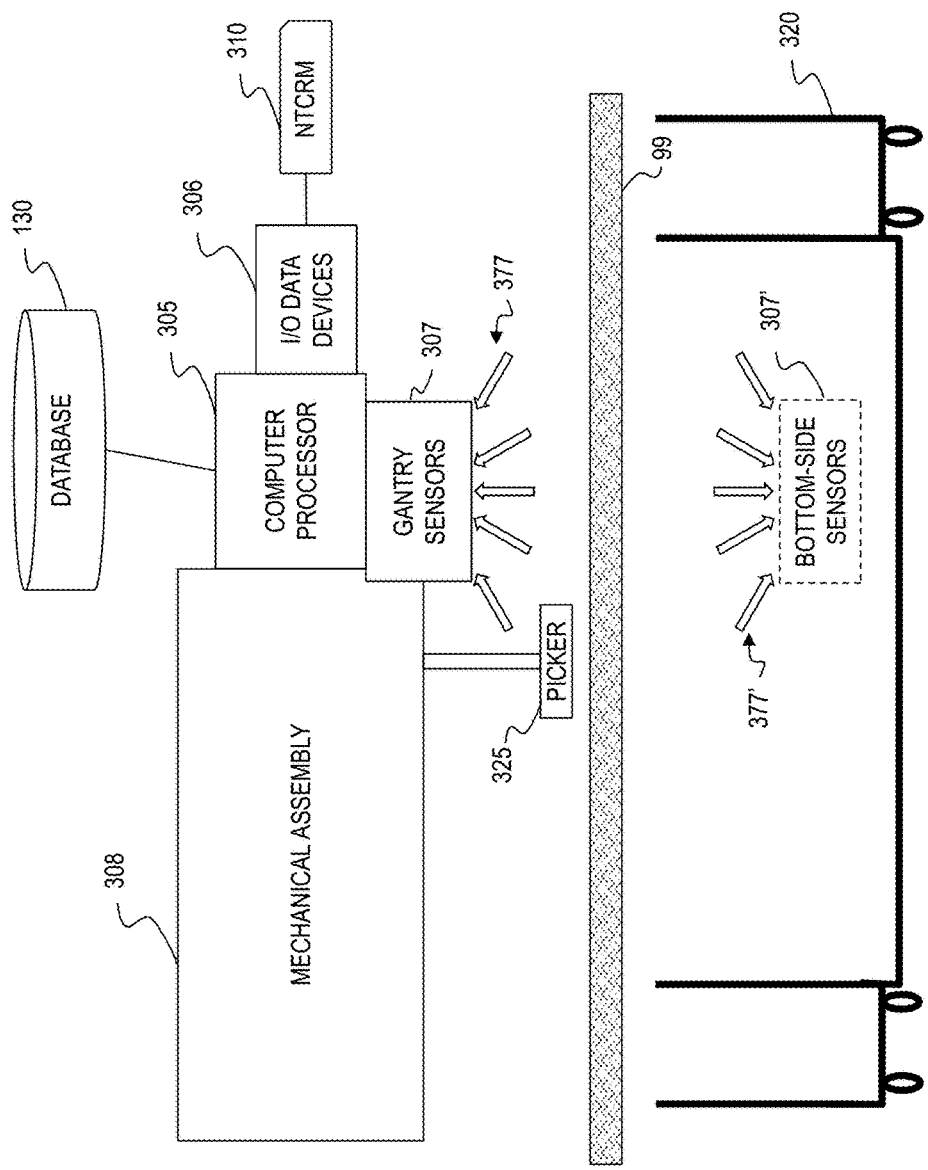
FIG. 3A is a side-view schematic diagram of a lumber-analyzer system 301, according to some embodiments of the present invention.

FIG. 3A is a side-view schematic diagram of a lumber-analyzer system 301, according to some embodiments of the present invention. In some embodiments, system 301 includes a computer processor 305 (in some embodiments, a Raspberry Pi® is used for processor 305 and is located on gantry 308, and uses open-source software (e.g., OPENCV) that has box, line, and color detection as well as knot and crack detection, where sometimes wane shows better in images from a visual sensor due to the color of bark), wherein computer processor 305 includes a plurality of input/output data devices 306 and a plurality of gantry sensors 307 that obtain image and/or distance data 377 from the top of lumber 99 on cart 320, and/or bottom-side sensors 307' that obtain image and/or distance data 377' from the bottom of a piece of lumber 99 that has been removed from a cart 320 (e.g., in some embodiments, one of a plurality of such carts 320-321) as the piece of lumber is being moved toward the rejection station 370, the flip station 380 and/or the saw station 390 (see FIG. 3B). In some embodiments, system 301 further includes a mechanical assembly 308 integrated with computer processor 305 to grab (using picker assembly 325) and reposition a piece of wood lumber 99 based on software code executing in computer processor 305 that processes the point location data received from gantry sensors 307 and/or bottom-side sensors 307'. In some embodiments, a database 130 (containing criteria-and-action data for each one of a plurality of end products to be made from the lumber, such that when a piece of lumber conforms to certain criteria, certain particular actions are carried out) is operatively coupled to computer processor 305. In some embodiments, a non-transitory computer-readable medium 310 (storing thereon instructions for performing the method of the present invention) is connectable to computer processor 305, for example, via one or more of the plurality of input/output data devices 306.

Figure 3B:
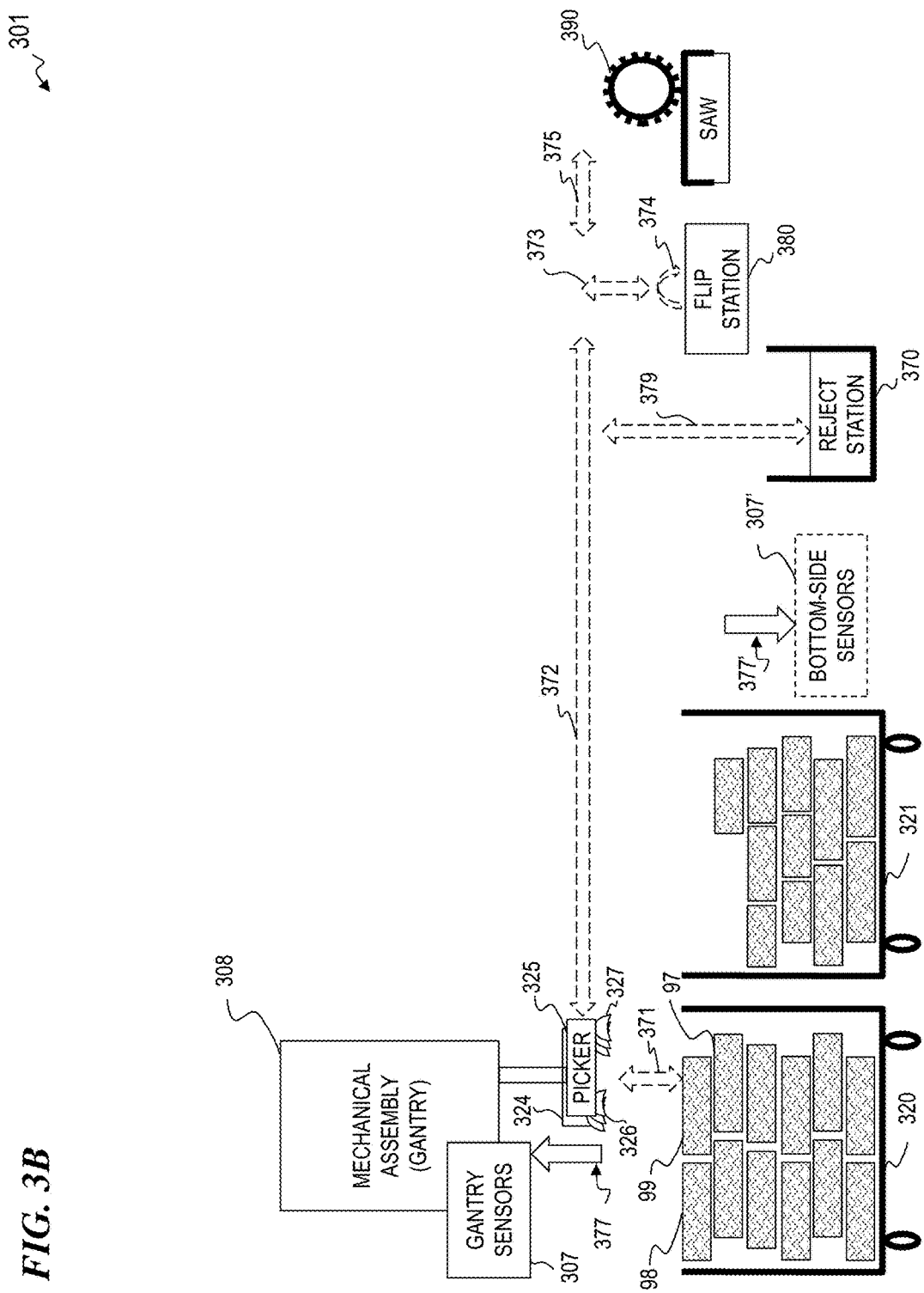
FIG. 3B is an end-view schematic diagram of lumber-analyzer system 301, according to some embodiments of the present invention.

FIG. 3B is an end-view schematic diagram of lumber-analyzer system 301, according to some embodiments of the present invention, which, for convenience, illustrates the processing of lumber where the lumber is moved left-to-right in the figure. In some embodiments, only top-side gantry-located sensors 307 are used, while in other embodiments, only bottom-side sensors 307' are used, while in yet other embodiments, both top-side gantry sensors 307 and bottom-side sensors 307' are used. In some embodiments, the mechanical assembly (e.g., the gantry) 308 has (in addition to the gantry sensors 307 if used) a single board-picker mechanism 325 that is used and carries one board at a time (from left-to-right in the FIG. 3B), while in other embodiments, gantry 308 has (in addition to the gantry sensors 307 if used) a plurality of board-picker mechanisms 324-325 that are each used to carry one or more boards at a time (from left-to-right in the FIG. 3B). In some embodiments, gantry 308 is operable to pick one or more boards from each of one or more of a plurality of carts 320-321 (only two of which are shown here).

Continuing to refer to FIG. 3B, in some embodiments that use only top-side gantry-located sensors 307, a board 99 is scanned or imaged by gantry sensors 307 to determine the position and orientation of board 99 in absolute terms and/or in relation to other boards 97 and 98. In some embodiments, the points along the edges and top surface of board 99 are determined and distinguished by the height difference relative to the points detected of a lower board 97. In some embodiments, the points along the edges and top surface of board 99 are determined and distinguished by the brightness differences of the boards relative to the spaces between top board 99 and top board 98. In some embodiments, the points along the edges and top surface of board 99 obtained from top-side gantry-located sensors 307 are used to position picker(s) 324 and/or 325 in order to pick up board 99 (and/or simultaneously pick up board 98). Based on the geometry data obtained from the top-side gantry-located sensors 307, the board 99 is picked up by path 371, carried along path 372, possibly dropped along path 379 to rejection station 370 (in the case where system 301 and method 101 have determined that the current processing stations are not able to accommodate the detected flaws in the board), or deposited on flip station 380 by path 373 and/or taken to saw station 390 by path 375. In some embodiments, if the board is deposited on flip station 380, it is flipped over along path 374 (rotated 180 degrees around its long axis) and then the opposite side is inspected by gantry sensors 307 (or the board is picked up by picker(s) 324-325 and transported back over the bottom-side sensors 307' to perform the detailed inspection of the side not originally inspected during the first pass over sensors 307'), and based on the inspection of the opposite side, the now doubly-inspected board is dumped at reject station 370 or transported and placed on saw station 390.

In some embodiments, system 301 uses its detection of the crown face (which typically has only one "high" point) of a crooked board to place the side opposite the crown face (which typically has two "high" points) against the saw fence of saw station 390 so the board is more stable and does not move as the board is being sawed. Flip station 380 facilitates this positioning.

In some embodiments, system 301 uses method 101 to elicit and receive optical and/or XYZ point locations data (geometry data regarding the surfaces and edges of the lumber) to detect and measure wane or cracks on the board (see FIG. 2D). In some embodiments, system 301 detects cup defects (see FIG. 2F). In some embodiments, the system 301 detects crook defects (see FIG. 2A) and determines the crown face of the board. In some embodiments, system 301 further performs wane detection and/or split detection (see FIG. 2D), knot detection (see FIG. 2E), and/or bark detection (see FIG. 2D).

In some embodiments, system 301 detects other data (non-geometry data) such as grain quality and ring density. In some embodiments, these parameters are determined by one or more video cameras and one or more machine-vision algorithms applied to images obtained from the camera(s).

In some embodiments, system 301 reorients the lumber by mechanical action, physically flipping the lumber piece around its longest axes and/or rotating the lumber piece on one of its short axes to better optimize wood position. In some embodiments, reorientation of the lumber is accomplished using compressed air; for example, by placing the piece of lumber on a surface (of flip station 380) having a plurality of holes through which compressed air is selectively applied in a short burst along one edge to flip the board around its longest axis. In some other embodiments, reorientation of the lumber uses mechanical clamps or fasteners, such as a clamping device that grabs opposite faces of the piece of lumber, or a piercing device that screws or pierces to grab the lumber and flip the board around its longest axis.

Figure 4A:
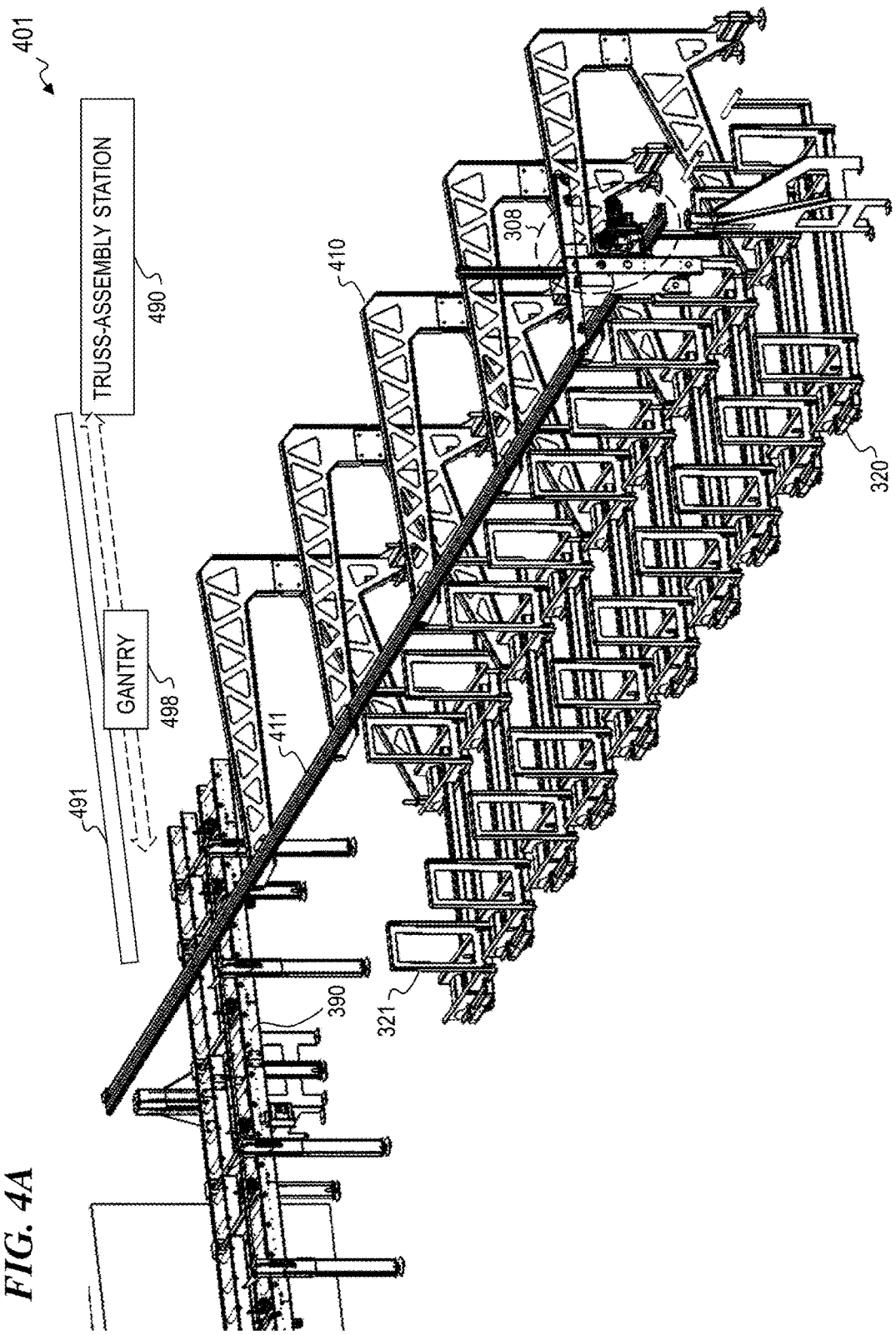
FIG. 4A is a perspective view of a lumber-analyzer system 401, according to some embodiments of the present invention.

FIG. 4A is a perspective view of a lumber-analyzer and processing system 401, according to some embodiments of the present invention. In some embodiments, system 401 includes a plurality of lumber-carrying carts 320-321 (ten such carts are shown here), and gantry 308 conveys one or more pieces of lumber 98-99 from one of the carts 320-321 eventually to saw station 390 in the upper left of the diagram of FIG. 4A. In some embodiments, gantry 308 travels along track 411 that is supported by a plurality of cantilevered arms 410, and which runs at right-angles to track 411. In some embodiments, bottom-side sensors 307', as well as stations 370 and 380 of FIG. 3B (not shown here for simplicity) are located between end cart 321 and saw station 390. In other embodiments, bottom-side sensors 307', and stations 370 and 380 of FIG. 3B are located at other suitable positions. In some embodiments, another conveyor system using track 491 and gantry 498 picks up and moves the sawn lumber pieces from saw station 390 to a truss-assembly station 490 (for example, such as described in U.S. Provisional Patent Application 62/144,859 by Steven Weinschenk, and U.S. patent application Ser. No. 15/093,732 filed Apr. 7, 2016 by Steven R. Weinschenk et al., titled "DIGITAL PROJECTION SYSTEM AND METHOD FOR WORKPIECE ASSEMBLY"; and/or the other patents and patent publications described in the background section above, which are incorporated herein by reference in their entirety).

In some embodiments, one or more human users 90 communicate with system 301 or 401 via wireless communications such as one or more of the devices 110 of FIG. 1. In some such embodiments, human users 90 communicate with system 301 or 401 via wireless mobile devices 123, 124, 125 and/or 127.

Figure 4B:
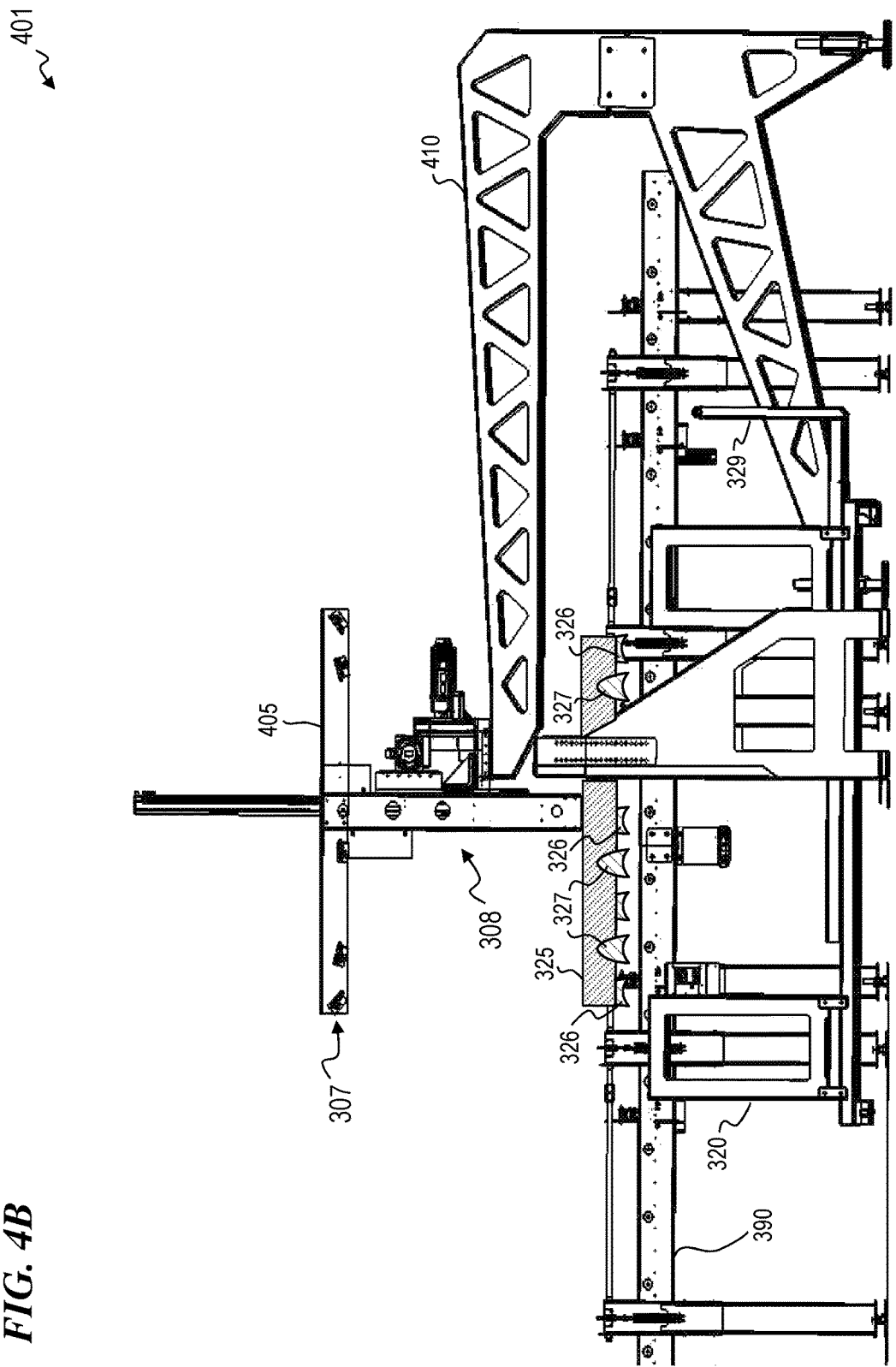
FIG. 4B is a side-view of lumber-analyzer system 401, according to some embodiments of the present invention.

FIG. 4B is a side-view of system 401, according to some embodiments of the present invention. The various parts and features are as described above for like reference numbers. In some embodiments, the gantry sensors 307 are mounted on sensor arm 405. In some embodiments, the cart handles 329 are located on the opposite end of cart 320 as shown in FIGS. 4A and 4B, such that human workers can pull empty carts out towards the left and replace the removed empty carts with carts full of lumber pieces by pushing the replacement carts into position in a left-to-right direction relative to this figure.

FIG. 4C is a front-end view of system 401, according to some embodiments of the present invention. The various parts and features are as described above for like reference numbers.

FIG. 4D is a back-end view of system 401, according to some embodiments of the present invention. Again, the various parts and features are as described above for like reference numbers.

Figure 4E:
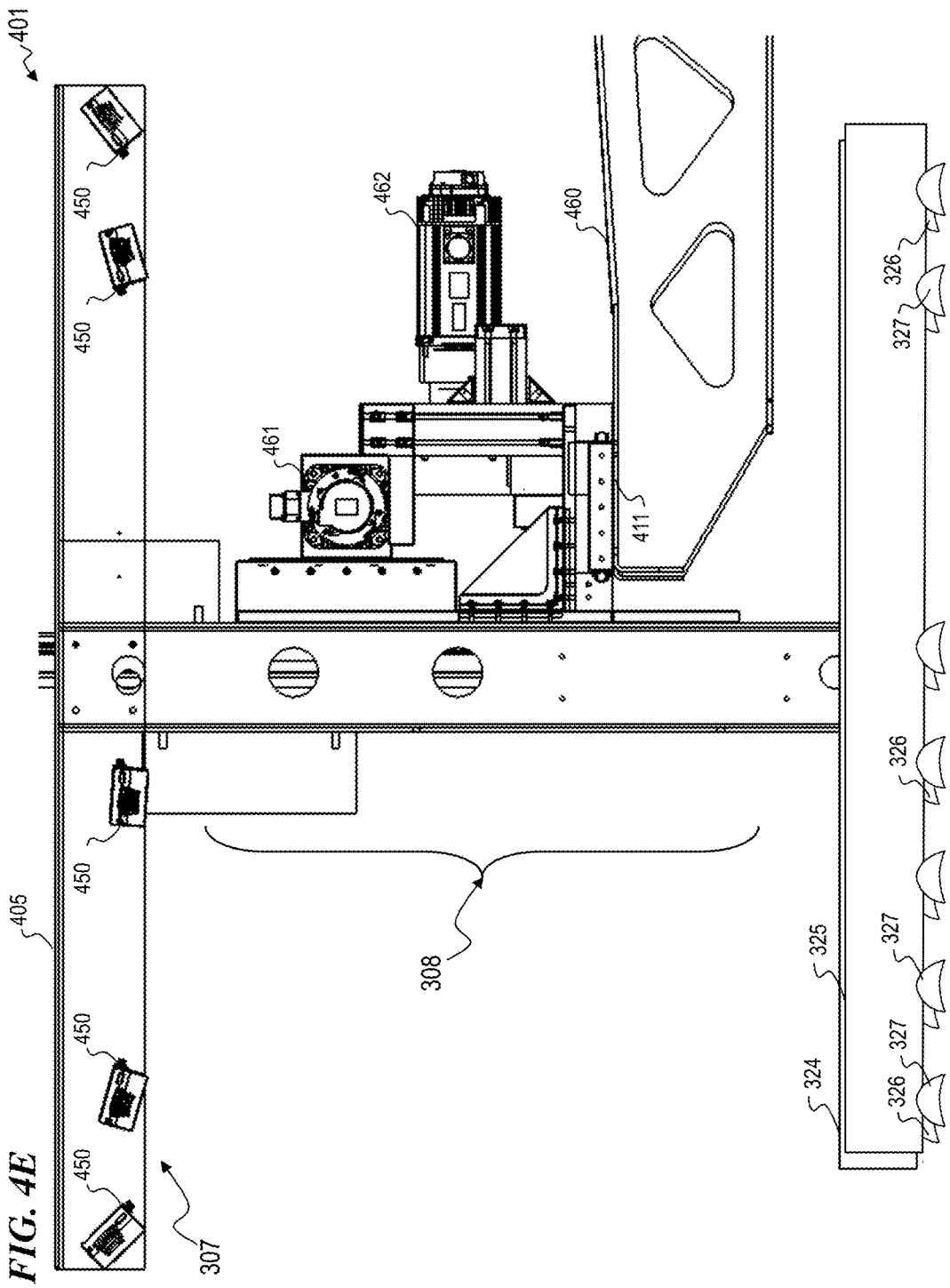
FIG. 4E is a close-up side-view schematic diagram of a lumber-analyzer system 401, according to some embodiments of the present invention.

FIG. 4E is a close-up side-view schematic diagram of a portion of system 401, according to some embodiments of the present invention. In some embodiments, system 401 uses gantry sensors 307 that include a plurality of distance sensors 450 mounted to arm 405 at a plurality of spaced-apart locations and angled orientations situated to sense both ends and a plurality of intermediate positions of boards up to about 20 feet (about 6 meters) long. In some embodiments, five point sensors are used, and the system is calibrated to convert the distance parameter from each sensor (which is at a given angle and sensor height, and a known Z-position of the gantry 308 along track 411) to the X, Y, and Z coordinates of each point measured. In other embodiments, a 3D sensor (e.g., the O3D302 sensor from IFM Efector, Inc., 1100 Atwater Drive, Malvern, Pa. 19355) measures XYZ coordinates of a plurality of locations substantially simultaneously (e.g., up to 64 or more points at each time a measurement is taken (e.g., in some embodiments, up to four or more times per second)). In some embodiments, track 411 is mounted on arm 460, and motor 461 moves one or more pickers 324-325 up and down, while motor 462 is used to move gantry 308 and sensors 307 together along track 411 (in a direction that would be towards or away from the surface of FIG. 4E). In some embodiments, picker 324 includes a plurality of suction (vacuum) operated attachment units 326, and picker 325 includes a plurality of suction (vacuum) operated attachment units 327. In other embodiments, other picker modalities are used (such as piercing points or screws that penetrate the piece of lumber, or clamping jaws that grab and hold the lumber).

FIG. 5A is a schematic diagram of a lumber-analyzer and processing system 501, according to some embodiments of the present invention. In some embodiments, system 501 includes a gantry 308 that moves in and out relative to a plurality of stacks of lumber, each located on one of a plurality of bunks 528 (in the embodiment shown here, each bunk uses a shelf 529 to support its stack of lumber; in other embodiments, a plurality of cantilevered arms extending perpendicular to the long axes of the boards are spaced apart along the length of the boards and facilitate loading the bunks using a forklift or similar machinery). that are vertically displaced relative to one another, in contrast to stacks of lumber that are horizontally displaced relative to one another as shown in FIGS. 4A-4E. In some such embodiments, the picker 324 moves left-and-right relative to the figure to reach in above a selected one of the plurality of stacks of lumber 520-521, where one or more stacks of lumber 520-521 are placed on a plurality of vertically displaced shelves 529. A Y-track 537 is used to move the gantry 308 vertically to a selected one of the plurality of shelves 529 and its stack(s) of lumber 520-521, where a picker 324 (e.g., in some embodiments, using suction grippers) picks up a board that has been measured (as described above, for crook, bow, twist, cup, cracks and/or knots and the like), and delivered to flipper 380 and/or saw 390, or to the reject station 370. Thus, in some embodiments, gantry 308 moves up-down to one of plurality of stacked bunks (using shelves 529 or other suitable supports) of lumber stacks 320-321. Gantry 308 moves left-right over selected stack (e.g., 321) of lumber, picks a selected board 99, and camera/scanner 307 measures crown, bow, twist, wane, color, grade. Gantry 308 moves back-forth using tracks 538 and 539 between the stacked bunks 528 and saw input table of saw unit 390 (or flipper 280 or the discard pile of the reject unit 370).

Figure 5B:
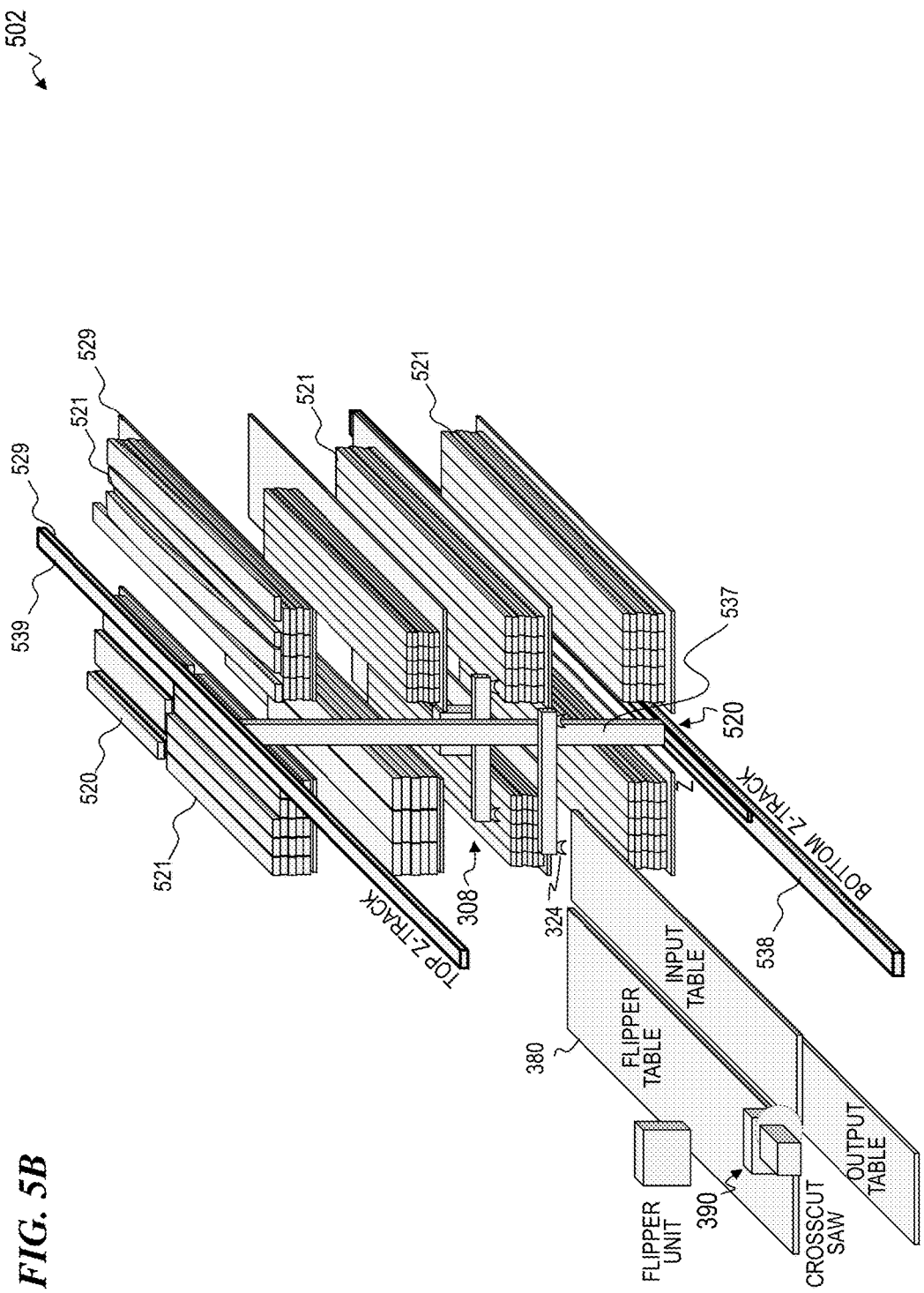
FIG. 5B is a schematic diagram of a lumber-analyzer system 502, according to some embodiments of the present invention.

FIG. 5B is a schematic diagram of a lumber-analyzer system 502, according to some embodiments of the present invention. In some embodiments, system 502 is similar to system 501 described above, but has sets of bunks of lumber that are vertically displaced on both of the two sides of a centrally positioned gantry-movement system. Thus, in some embodiments, gantry 308 moves up-down to one of plurality of stacked bunks (using shelves 529 or other suitable supports) of lumber stacks 320-321. Gantry 308 moves left-right over selected stack (e.g., 321) of lumber, on the LEFT SIDE OR RIGHT SIDE of the central gantry-movement system 520, and picks a selected board 99, and camera/scanner 307 measures crown, bow, twist, wane, color, grade. Gantry 302 moves back-forth using tracks 538 and 539 between the two sets of stacked bunks and saw input table of saw unit 390 (or flipper 280 or the discard pile of the reject unit 370).

Figure 6:
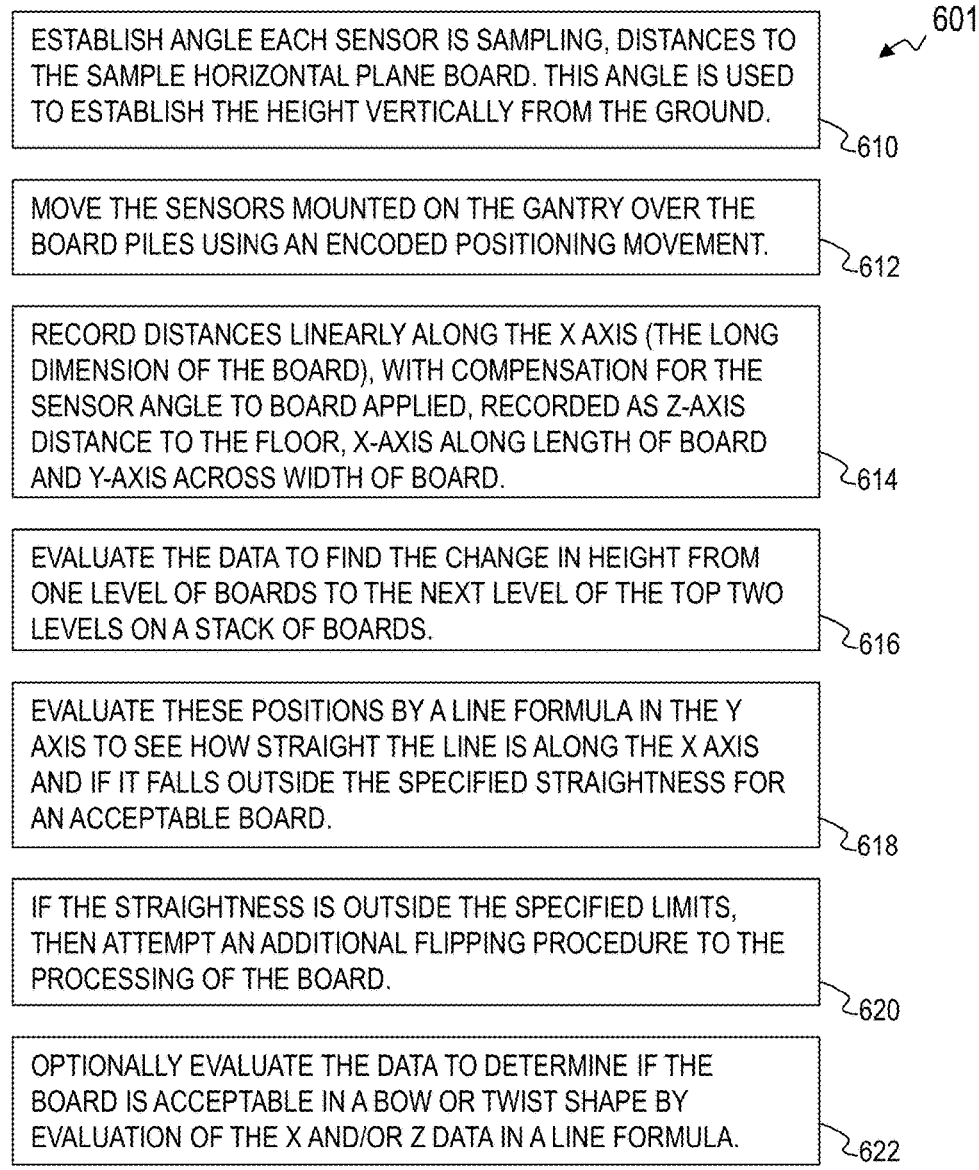
FIG. 6 is a flowchart of a method 601, according to some embodiments of the present invention.

FIG. 6 is a flowchart of a method 601, according to some embodiments of the present invention. In some embodiments, method 601 includes block 610 that establishes the angle each sensor is sampling and the distances to the sample horizontal plane board (this angle is used to establish the height vertically from the ground); block 612 that moves the sensors mounted on the gantry over the board piles using an encoded positioning movement; block 614 that records distances linearly along the x axis (the long dimension of the board), with compensation for the sensor angle to board applied (to change from a linear distance at angle to XYZ coordinates of each point measured), recorded as Z axis distance to the floor, X axis along length of board and Y axis across width of board; block 616 that evaluates the data to find the change in height from one level of boards to the next level of the top two levels on a stack of boards (in order to distinguish where the edge of the board is the transition from one plane to the next indicates the edge of the board at five or more locations, which determines whether the board is straight or curved); block 618 that evaluates these positions using a line formula in the Y axis to see how straight is the line along the X axis and if it falls outside the specified straightness for an acceptable board; block 620 that, if the straightness is outside the specified limits, then attempts an additional flipping procedure to the processing of the board (to ensure that the proper edge (e.g., the outside or crown edge) of the board is on the desired side of the saw table (e.g., the side of the table towards or away from the fence in a cross-cut saw)); and block 622 that optionally evaluates the data to determine if the board is acceptable in a bow or twist shape by evaluation of the x and/or z data in a line formula. In some embodiments, the present invention provides a vacuum picker, a screw picker, a hook picker, a clamp picker, a piercing picker, or a picker that incorporates a plurality of such modalities. In some embodiments, a dual picker includes two sets of vacuum pick heads, each set able to pick a separate board. In some embodiments, if twist or cupping is detected, the system may reject the board. In some embodiments, wane boards are lower grade and the system can pick through the boards and sort relative to criteria that indicates "OK for some uses." In some embodiments, the sensors 307 are all on the top of the gantry. In some embodiments, another set of sensors 307' is looking up to detect wane, bow, etc. from underneath. In some embodiments, sensors 307' are an alternative to top-side sensors 307 or in other embodiments, they are an additional set of sensors. When used, sensors 307' scan the underneath side of boards on the picker 325. In some embodiments, the boards are put on flipping station 380 before re-grabbing to put onto saw station 390.

In some embodiments, the home position for each of the plurality of carts 320-321 includes a centering track and an end stop that facilitates locating of the cart so the system 301 can more easily locate the cart and its stack of lumber.

FIG. 7A is a schematic block diagram of a vacuum-activated lumber picker suction-cup assembly 701, according to some embodiments of the present invention. In some embodiments, suction-cup assembly 701 includes a pliant supple rugged suction-cup 710, a Venturi assembly 712, a compressed-air source 720, and a controller 730 (such as a computer processor, for example a Raspberry Pi® or the like). In some embodiments, controller 730 controls a plurality of valves (e.g., 713 and 716) to generate a vacuum for suction cup 710 and/or to release the vacuum or blow away sawdust or other debris. In the exemplary embodiment shown, controller 730 opening valve 713 releases compressed air 714 into Venturi assembly 712, which causes a lowered air pressure (a partial vacuum) in connector 711, which removes air from suction cup 710. When the suction cup 710 is seated on a piece of lumber and compressed air 714 is forced through the Venturi assembly 712, the surrounding air pressure (which is higher than the air pressure in the suction cup 710) holds the piece of lumber against the suction cup, which allows the picker to lift and move the piece of lumber. In some embodiments, when controller 730 sends a signal to cause valve 716 to open, compressed air is fed into vacuum cup 710, which serves either or both of two purposes: to initially blow away sawdust or other debris from the piece of lumber, and/or to quickly release the piece from the suction cup 710. In some embodiments, the waste air 715 from Venturi assembly 712 is directed over the tops of the suction cups 710 (not shown here) to keep the assembly clean, or is discarded (as shown here). In some embodiments, a sensor 740 is used to detect and/or measure an amount of excess pressure and/or reduced pressure (i.e., vacuum) in suction cup 710, and to provide a feedback signal 741 that is received by controller 730 to adjust its operation of valves 713 and/or 716. For example, if the vacuum in a particular suction cup 710 is not developed and maintained when its respective valve 713 is opened (as would be expected), the controller can determine that:

(A) if no suction cup sensor 740 indicates vacuum, then the piece of wood has not been picked up during the initial try so the picker head goes back to try again (optionally using slightly different positioning);

(B) if some suction cup sensors 740 previously indicated vacuum but now none do, then the piece of wood has been dropped some other place along its path and a human may need to go pick it up;

(C) if some suction cup sensors 740 indicate vacuum but others do not, then the piece of wood is being held, but perhaps as a defect such as a crack or wane in the vicinity of the suction cups lacking vacuum—likewise a rough estimate of the length of the lumber can be obtained if the suction cups 710 near the end(s) are not showing vacuum due to the piece of lumber being too short to reach them;

(D) the valves 713 and or 716 can be partially closed such that the vacuum is slowly released when the piece of lumber has nearly reached its destination (i.e., held perhaps 1-2 cm above where it is to be deposited), such that the weight of the piece of lumber can be calculated by using the known area of each suction cup that had vacuum, the value of the pressure signal(s) in the suction cups 710 just before all vacuum was lost, the value of air pressure in the surrounding room, the number of such vacuum cups 710 having vacuum, and the fact that vacuum was suddenly lost when the piece of lumber was dropped; and/or (E) other similar determinations.

FIG. 7B is a schematic side-view block diagram of a vacuum-activated lumber picker assembly 702 that includes a plurality of suction-cup assemblies 701 attached to a pickup arm 722 (e.g., in some embodiments, a steel beam), according to some embodiments of the present invention. In some embodiments, vacuum-activated lumber picker assembly 702 has its plurality of suction-cup assemblies 710 arranged in a staggered-row or zigzag-row configuration, such that if the piece of lumber has a defect such as a knot, crack or the like, or its position has been misidentified in such a way that prevents all or most of the suction cups 710 in one row from achieving sufficient vacuum to pick up the piece of wood, then the others of the suction cups 710 may still be able to achieve a strong hold on the piece of lumber. In some embodiments, the suction cups 710 of one staggered row are alternately spaced on either side of a center line. In some such embodiments, the suction cups 710 are all spaced the same distance from the centerline, while in other embodiments, a plurality of different spacings are used. In some embodiments, a plurality of staggered rows of suction cups 710 are provided for each picker, in order that the picker can simultaneously hold up to N pieces of lumber (e.g., two, three, or more pieces at the same time). In some embodiments, the pieces of lumber on a source pile of lumber may be at a single height when the picker arrives, and so a plurality of pieces can be picked up at the same time; at other times, the pieces of one pile could be at different heights, and so the picker would then pick up a single board at a time (e.g., the top-most board is grabbed by one staggered row of suction cups 710, then the picker arm is moved to the side so that a different staggered row of suction cups 710 picks up a second and/or third piece of lumber), and the picker then moves that plurality of lumber pieces to their destination(s) and there deposits the plurality of lumber pieces one-at-a-time or all-at-once to be sawed or otherwise processed. In some embodiments, the system may drop a first piece of lumber onto a flipper 380 to be flipped over, then pick up the first piece of lumber from flipper 380 and then drop a second piece of lumber onto a flipper 380, then pick up the second piece of lumber from flipper 380 and move to the saw 390 where the picker assembly 702 deposits the plurality of pieces of lumber one-at-a-time or all-at-once.

In some embodiments, the system optionally chooses to pick up a piece of lumber from flipper table 380 or from saw 390 and take that piece of lumber back to rejection station 370 or to one of the "source" piles of lumber on carts 320-321.

FIG. 7C is a perspective view of a vacuum-activated lumber picker assembly 703 that includes a plurality of suction-cup assemblies 701 arranged in two staggered rows 704 and 705 on a single picker arm, according to some embodiments of the present invention. In some such embodiments, each suction cup 701 is a rounded-end elongated approximately rectangular or pill-shaped shape, with a length in the direction of the long axis of the piece of lumber being greater than its width (e.g., in some embodiments, the length of each suction cup 701 is between about two times the width to four times its width). In some embodiments, the width if the lip on the interface surface around the rim of each suction cup 701 is between about 1 cm and about 3 cm. In some embodiments, lumber picker assembly 703 includes a motorized actuator 723 to lower and raise the pickup arm 722, and one or more scanners 721 used to locate and/or measure each piece of lumber to be picked up.

Figure 8:
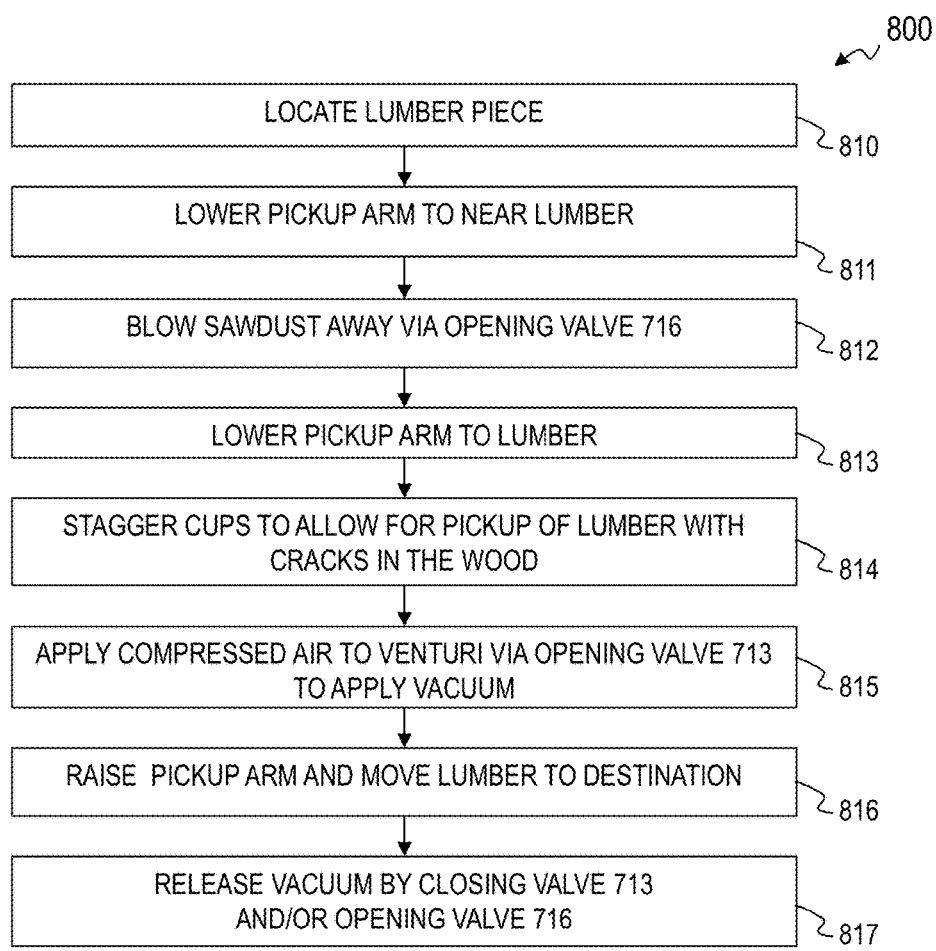
FIG. 8 is a flowchart of a lumber-picker method 801, according to some embodiments of the present invention.

FIG. 8 is a flowchart of a lumber-picker method 801, according to some embodiments of the present invention. In some embodiments, method 801 includes:

locating 810 and selecting the lumber piece to be picked up;

lowering 811 the pickup arm 722 so that the suction cups 701 are near but not seated on the piece of lumber (e.g., in some embodiments, about 5 mm to 25 mm above the piece of lumber);

blowing 812 sawdust or other debris away using compressed air released either through or around the suction cups 701 (e.g., by opening one or more valves 716 to a plurality of suction cups 701);

seating 813 the suction cups 701 on the surface of the selected piece of lumber; e.g., by further lowering the pickup arm 722 until the lips of the suction cups are resting or pressed against the selected piece of lumber;

staggering 814 the positions of the suction cups 701 on the pickup arm 722 that are to be activated (either by positioning the suction cups 701 in a staggered-row configuration, or by using a larger plurality of suction cups 701 and opening only those valves 713 and/or 716 to those selected ones of the suction cups 701 that are along a staggered row);

applying 814 compressed air to a plurality of Venturi assemblies 712 associated with the selected ones of the suction cups 701 in order to apply vacuum (reduced pressure) to those respective ones of the suction cups 701;

raising and moving 816 the pickup arm to move the piece of lumber to its destination; and releasing 817 the piece of lumber by releasing the vacuum (closing valves 713) and/or applying compressed air (opening valves 716).

In some embodiments, the present invention provides a method and system that performs one or more of the following procedures:

scans or images a pile of lumber;

determines whether one or more boards is acceptable as is or if it/they need reorientation;

orients the board such that the crown of this board matches (is oriented in the same direction as the crown of another board in the truss or wall section being assembled) or complements (is oriented to compensate for the crown of another board that is oriented in a different direction) another board in the item being assembled;

detects the dimension (whether 2×4, 2×6, 2×8, or other dimension) of a selected board (which is particularly useful if boards of different dimensions are mixed in a pile held by a cart or bunk, or when several piles are available and someone changes carts or the operator does not want to enter the data by hand for each cart), wherein in some embodiments, the system detects indents between boards in an image and measures the width of each board;

measures how high a stack of 2×4's is and uses the height and width to determine how many pieces of lumber are in the pile; and/or determines whether there are enough pieces of lumber for the current job.

In some embodiments, if there are ten carts in a row (each cart holding a plurality of pieces of lumber), each time the machine returns to a cart, the system re-scans the cart (in case a person has moved the cart, or added or removed boards, or some other change has occurred), picks up a board and delivers the board to the saw machine or to the flipper machine.

In some embodiments, the measurement and determination of the geometry (curves, bow, crown direction and the like) is performed while the board is on a cart 320 or bunk 528, and/or held by a picker on the gantry 308, and/or on the flipper station 380.

In some embodiments, the sensors include multiple single-point distance sensors (e.g., analog distance sensors such as a model VDM28-8-L-IO/110/115b/122 distance sensor available from Pepperl and Fuchs; www.pepperl-fuchs.com), which provide outputs wherein a perfectly straight board trips all the sensors at the same time. Sometimes, if a board is diagonally oriented or skewed (for example, as a result of a person hand throwing lumber in pile), then the vacuum pickups cannot pick up the board. As sensors go over the board, the sensors trip in sequence (at different times) so the board is determined to be straight but skewed on the pile. In other embodiments, instead of analog sensors, the system 301 or 401 uses a video camera and filters the image data to find the data needed (for example, the color of the lumber can be used to determine whether each board is treated (e.g., with anti-rot chemicals) or not treated) and to determine length (in some embodiments, the method and system use OPENCV open-source software to analyze the images). In some embodiments, the user will retrofit the machine by adding a camera. The system then archives (stores into an image database) the images of each board that go into each product being assembled, so that if a defect is later discovered in a truss, a forensic investigator can tell when that board, for example, got cracked (before, during or after assembly). Some embodiments further include one or more Kinect®-type 3D sensor-and-camera subsystems. Such scanners may cost only about $2000, and the scanner can get a 3D profile to measure how much wane is missing on a board (for example, if the wane is only on three feet of a 20 foot-board, the system can cut pieces to maximize the value obtained from pieces of that board, thus, cumulatively, obtaining much greater value than the cost of the 3D sensor).

In some embodiments, the system 301 or 401 includes an image projector that projects an image onto the work surface of saw machine 390 (similar to projection systems such as described in co-pending U.S. patent application Ser. No. 15/093,732 filed Apr. 7, 2016 by Steven R. Weinschenk et al., titled "DIGITAL PROJECTION SYSTEM AND METHOD FOR WORKPIECE ASSEMBLY"; which is incorporated herein by reference in its entirety), then notifies the human operator to reposition a board on the saw machine work surface according to the projected image. This is particularly useful for unusual situations where the system has difficulty correcting for a particular defect in a board such that intervention from a human is needed to move the board on the saw so it can be properly cut.

In some embodiments, system 301 or 401 uses one of the sensors 307 to scan reloaded carts for barcodes on the lumber or other indicia such as a barcode on wrapping paper. The scanned barcode information goes into the gantry's computer system and is communicated to the system processor. In some embodiments, a smartphone scan by the operator is wirelessly communicated into the gantry system to collect barcode from carts and barcodes from lumber wrapper, and correlate the barcode from the wrapper to the barcoded cart holding lumber previously in that wrapper. In some embodiments, for a grade stamp that is only on a board, or alternatively on the wrapper, in text, the system 301 or 401 reads those characters and performs OCR (optical character recognition) to get the grade of every board. In some embodiments, system 301 or 401 flips a piece of lumber to get an image of the grade stamp on that board.

In some embodiments, system 301 determines the length of each board, which is needed because operators sometimes throw boards on an incorrect pile by mistake.

In some embodiments, system 301 or 401 includes a projector system (such as SteadyShot™, or such as described in co-pending U.S. patent application Ser. No. 15/093,732 filed Apr. 7, 2016 by Steven R. Weinschenk et al., titled "DIGITAL PROJECTION SYSTEM AND METHOD FOR WORKPIECE ASSEMBLY" which is incorporated herein by reference in its entirety) that has previously been used for roof trusses, but in the present system is now also used for wall panels, studs, windows, cripple studs and the like. In some embodiments, the system then takes a picture of the wall before putting sheeting or sheathing (e.g., gypsum drywall, exterior plywood siding or the like) on it when building a wall section. Conventional systems and methods using a power nailer assumed studs were straight (not bowed), so nails would miss certain studs if the studs were bowed. To remedy this, some embodiments of the present system take a digital image of the assembled stud product before sheathing is applied, and then use a projector system to project, onto the sheathing, the image of the studs taken before the sheathing is placed over the studs (so the human operator of the nailing gun can see exactly where the underlying studs are when nailing) and/or the predetermined nailing pattern for a particular wall panel, as automatically modified by pattern-recognition software based on the image of the studs taken before the sheathing is placed over the studs, where the projected image of the studs shows bowed studs that are hidden behind sheathing, providing a way for the user to nail into the bowed studs.

In conventional systems, the stacks of lumber are limited, both in size and in number, so that an entire job must be made from boards that have the same grade. In contrast, system 301, 401 or 501 can pick and choose boards from a pile containing different lengths and grades of lumber and select boards that are best suited (boards that are largely usable as-is) and/or modifiable (i.e., boards that can be cut in such a manner as to obtain a suitable piece of lumber for a particular use or location in the final product) to optimize the product being built. The optimization achieved by systems 301, 401 or 501 optionally includes such factors as strength, cost, aesthetic appearance, reduced work-in-process (WIP), speed of assembly, reduced factory size, just-in-time delivery, agile manufacturing (the ability to switch from the making of one end product to another end product), and/or the like.

In system 301 or 401, the gantry 308 works with horizontal boards that are piled on side-by-side carts 320-321. The horizontal spacing of the carts 320 takes lots of floor space. A factory often needs to pull equipment and other items out to put in a conventional cart-based system. In contrast, the new vertical picker of system 501 allows the picker and gantry to pick off boards from stacks that are on top of one another on bunks (shelves or other types of lumber holders).

In some embodiments, the saw stations 390 (of system 301, 401 or 501) cut pieces from 16-foot, 18-foot, and 20-foot boards, often the product needs a 6-foot board, and that leaves a 10-foot piece (or 12-foot or 14-foot piece), which, in some embodiments, the system picks up and puts back on one of the "incoming" piles of lumber on a cart 320 or bunk 528.

In some embodiments, system 501 (sometimes called a vertical air pick wood runner) has a new gantry 528 that moves horizontally in a direction parallel to the long axis of boards on single shelf that has 10-foot and 6-foot pieces end-to-end on the same cart 320-321 or bunk 528.

In some embodiments, system 301, 401 or 501 includes a "light-curtain" scanner to stop the machinery if people move into the way (providing a volume of space within which the machinery can move without harming a person). In some embodiments, the gantry moves up and out of way to allow a forklift to gain access to load wood onto a bunk 528.

In some embodiments, the present invention includes a 24-foot long "rip" saw operatively coupled to the infeed of a cross-cur saw station 390, wherein the rip saw slices a board end-to-end parallel to its long axis (e.g., to cut a 2×8 board into a 2×6 board and a 2×2 board).

In some embodiments, system 502 has a gantry 308 that picks boards from bunks on either side of the lengthwise path of the gantry motion system.

In systems that have ten bunks on carts that are horizontally spaced, the system takes lots of floor space. In some embodiments, system 502 includes a plurality of sets of bunks, wherein each set of eight bunks has its own gantry (e.g., a four-high double-sided organization). In some embodiments, system 501 or 502 includes a further set of vertically spaced-apart bunks spaced lengthwise (i.e., a plurality of vertically spaced-apart bunks in each of a plurality of such sets spaced lengthwise) at a distance further from the saw station 390 as the set shown in FIG. 5A or FIG. 5B. In some embodiments, system 501 or 502 includes a further set of bunks spaced lengthwise on the opposite end of the saw station 390 as the set shown in FIG. 5A or FIG. 5B.

In summary, some embodiments include: 1) Crown detection scanner and image camera that analyze the boards from gantry 308 or a fixed table (such as flip table 380), optionally including lasers and/or scanners and/or cameras for detecting size and number of pieces and length and color and grade marks of the boards; 2) a bar-code scanner system that correlates the original pack (the wrapped pile of lumber) and the cart to which the pile was loaded, in order that the cart bar code can be used to look up the bar code of the wrapper; 3) an OCR or other optical text reader that determines the grade(s) of the boards; and/or 4) a vertical wood runner (such as system 501 or 502) that uses vertically stacked bunks 528.

In some embodiments, the present invention provides a system that includes a computer processor that includes: a plurality of data-input devices, a plurality of data-output devices, and a plurality of sensors; and a mechanical assembly integrated with the computer processor to reposition a piece of wood lumber based on software code executing in the computer processor. In some embodiments, the system further includes a database operatively coupled to the computer processor (which, in some embodiments contains criteria-and-action data for each one of a plurality of end products to be made from the lumber, such that, after analyzing data for a plurality of pieces of lumber, when one of those pieces of lumber conforms to certain criteria, software code executing in the computer processor controls elements of the system to carry out particular actions).

In some embodiments, the present invention provides a method that operates on a computer processor having a plurality of data-input devices, a plurality of data-output devices, a plurality of sensors, a database, software code, and a wireless interface, wherein the computer processor is integrated with mechanical components, and wherein the method includes eliciting and receiving into the computer processor data parameters from a first human user; obtaining incoming data points about lumber from the plurality of sensors; processing the data parameters to obtain processed data parameters; storing the processed data parameters; comparing the incoming data points from the plurality of sensors to the stored data parameters to obtain comparison results; and conditionally directing the mechanical components to reject the lumber to a preprogrammed position based on the comparison results.

In some embodiments, the method further includes conditionally directing the mechanical components to feed the lumber into a saw assembly, as the lumber is currently positioned, based on the comparison results. In some embodiments, the method further includes conditionally directing the mechanical components to reposition the lumber to a more optimal position prior to feeding the lumber to a saw assembly based on the comparison results.

In some embodiments, the present invention provides a non-transitory storage medium having computer-executable instructions stored thereon, wherein the instructions, when executed on a suitable computer processor integrated with mechanical components and having a plurality of input data devices, a plurality of output data devices, a plurality of sensors, a database, software code, and a wireless interface, perform a method that includes eliciting and receiving into the computer processor data parameters from a first human user; obtaining incoming data points about lumber from the plurality of sensors; processing the data parameters to obtain processed data parameters; storing the processed data parameters; comparing the incoming data points from the plurality of sensors to the stored data parameters to obtain comparison results; and conditionally directing the mechanical components to reject the lumber to a preprogrammed position based on the comparison results.

In some embodiments, the non-transitory storage medium further includes instructions that cause the method to further include conditionally directing the mechanical components to feed the lumber into a saw assembly as positioned based on the comparison results. In some embodiments, the non-transitory storage medium further includes instructions that cause the method to further include conditionally directing the mechanical components to reposition the lumber to a more optimal position prior to feeding the lumber to a saw assembly based on the comparison results.

In some embodiments, the present invention provides a system for analyzing and manipulating a first piece of lumber, wherein the first piece of lumber is one of a plurality of lumber pieces on a lumber pile, the system including: a gantry structure; a lumber picker operatively coupled to the gantry structure; a lumber flipper; a saw unit; and a lumber-analysis unit operably coupled to the lumber picker, wherein the lumber-analysis unit is configured to analyze defects in the first piece of lumber and generate a lumber-defect result based on the analyzed defects, wherein the lumber picker and gantry structure are configured to move the first piece of lumber from the lumber pile to one of a plurality of destinations that includes the lumber flipper and the saw unit based on the lumber-defect result.

In some embodiments of the system, the lumber-analysis unit is further configured to determine a plurality of dimensions of the first piece of lumber.

In some embodiments of the system, the lumber-analysis unit is configured to analyze crook defects and to determine whether a board has a crook defect, and if so, which edge has a crown.

In some embodiments of the system, the lumber-analysis unit is configured to analyze twist defects, the lumber-analysis unit is configured to analyze bow defects, the lumber-analysis unit is configured to analyze knot defects, and/or the lumber-analysis unit is configured to analyze wane defects.

Some embodiments of the system further include a plurality of vertically spaced-apart lumber bunks, wherein the lumber picker and gantry structure are operatively coupled to pick a selected piece of lumber from a selected one of the plurality of vertically spaced-apart lumber bunks.

Some embodiments of the system further include a sets of lumber bunks, wherein each one of the plurality of sets includes a plurality of vertically spaced-apart lumber bunks, wherein the lumber picker and gantry structure are operatively coupled to pick a selected piece of lumber from a selected one of the plurality of vertically spaced-apart lumber bunks of a selected one of the plurality of sets.

In some embodiments of the system, when the lumber-defect result of the first piece if lumber is acceptable, then the lumber picker is configured to pick up the first piece of lumber from the lumber pile and deliver the first piece of lumber to a saw without reorienting the first piece of lumber.

Some embodiments of the system further include a lumber flipper configured to reorient lumber, wherein when the lumber-defect result is unacceptable, then the lumber picker is configured to pick up the first piece of lumber from the lumber pile and deliver the first piece of lumber to the flipper.

In some embodiments of the system, when the lumber-defect result is unacceptable, then the lumber picker is configured to pick up the first piece of lumber from the lumber pile and deliver the first piece of lumber to a discard pile of lumber.

In some embodiments of the system, the lumber picker includes a plurality of suction cups configured to grasp the first piece of lumber such that the first piece of lumber can be lifted off of the lumber pile and transported.

In some embodiments of the system, the lumber-analysis unit includes one or more optical sensors configured to optically scan the first piece of lumber in order to analyze defects in the first piece of lumber.

In some embodiments of the system, the lumber-analysis unit includes one or more cameras and a processor or controller, wherein the one or more cameras are configured to generate images of the first piece of lumber and electronically transmit the images to the processor, and wherein the processor is configured to compare the images to acceptable lumber images.

In some embodiments, the present invention provides an automated method for analyzing and processing lumber that implements the system described above.

In some embodiments, the present invention provides an automated method for analyzing and processing lumber that includes: providing a first plurality of lumber stacks, wherein each one of the first plurality of lumber stacks is vertically displaced relative to at least one other of the first plurality of lumber stacks; selecting a first lumber stack from the first plurality of lumber stacks; inspecting a first lumber piece on the first lumber stack and generating an analysis result based on the inspecting; picking up the first lumber piece from the first lumber stack; and transporting the first lumber piece to a processing location that is chosen based on the analysis result, wherein the transporting moves the first lumber piece in a direction that generally parallels a longitudinal axis of the first lumber stack.

In some embodiments of the method, the analysis result identifies the first lumber piece as unacceptable, and the transporting includes moving the first lumber piece to a discard pile.

In some embodiments of the method, the analysis result identifies the first lumber piece as requiring reorientation, and the transporting includes moving the first lumber piece to a lumber flipper configured to reorient the first lumber piece prior to further processing of the first lumber piece.

In some embodiments of the method, the analysis result identifies the first lumber piece as acceptable, and the transporting includes moving the first lumber piece to a saw station.

Some embodiments of the method further include: providing a second plurality of lumber stacks, wherein each one of the second plurality of lumber stacks is vertically displaced relative to others of the second plurality of lumber stacks, wherein the second plurality of lumber stacks is horizontally displaced relative to the first plurality of lumber stacks, and wherein the transporting includes moving the first lumber piece along a path that runs in between the first plurality of lumber stacks and the second plurality of lumber stacks.

In some embodiments of the method, the inspecting includes measuring a plurality of defect characteristics of the first lumber piece.

In some embodiments of the method, the inspecting includes measuring a plurality of dimensions of the first lumber piece.

Some embodiments of the method further include: providing a processor or controller operatively coupled to a plurality of user devices, a database, and a plurality of sensors; and eliciting and receiving acceptable lumber data from at least one of the plurality of user devices, wherein the inspecting includes gathering physical data of the first lumber piece using the plurality of sensors and storing the physical data in the database, and wherein the generating of the analysis result includes comparing the physical data to the acceptable lumber data using the processor.

Some embodiments of the method further include: after the picking up of the first lumber piece from the first lumber stack, inspecting the first lumber piece from a location below the first lumber piece.

In some embodiments of the method, the picking up of the first lumber piece includes applying a plurality of suction grippers to the first lumber piece.

In some embodiments, the present invention provides an apparatus for automated analysis and processing of lumber, the apparatus including: a first plurality of lumber bunks, wherein each one of the first plurality of lumber bunks is vertically displaced relative to at least one other of the first plurality of lumber bunks, and wherein each bunk is configured to hold a stack of lumber; means for selecting a first lumber stack from the first plurality of lumber bunks; means for inspecting a first lumber piece on the first lumber stack and generating an analysis result based on the inspecting; means for picking up the first lumber piece from the first lumber stack; and means for transporting the first lumber piece to a processing location that is chosen based on the analysis result, wherein the means for transporting moves the first lumber piece in a direction that parallels a longitudinal axis of the first lumber piece.

Some embodiments of the apparatus further include a second plurality of lumber bunks, wherein each one of the second plurality of lumber bunks is vertically displaced relative to others of the second plurality of lumber bunks, wherein the second plurality of lumber bunks is horizontally displaced relative to the first plurality of lumber bunks, and wherein the transporting includes moving the first lumber piece along a path that runs along the first plurality of lumber bunks and the second plurality of lumber bunks.

In some embodiments, the present invention provides an apparatus for manipulating a first piece of lumber, wherein the first piece of lumber is one of a plurality of lumber pieces on a lumber pile, and wherein the first piece of lumber has a first surface. This apparatus includes: a gantry structure that includes a raise/lower actuator; a lumber pickup arm operatively coupled to the raise/lower actuator of the gantry structure, wherein the lumber pickup arm includes a first plurality of selectively air-pressure-activatable suction cups arranged in a staggered configuration; a first plurality of air valves operably connected to the first plurality of suction cups; an optical location device configured to generate location parameters for where the first piece of lumber is to be picked up; and a controller operably connected to the first plurality of air valves and configured to control the raise/lower actuator to lower the lumber pickup arm based on the location parameters of where the first piece of lumber is to be picked up so that a first sub-plurality of the first plurality of suction cups seat on the first surface of the first piece of lumber, and to operate the first plurality of air valves so as to reduce air pressure in the first sub-plurality of the first plurality of suction cups to grab the first piece of lumber, and wherein the controller later increases air pressure in the plurality of the first plurality of suction cups to release the first piece of lumber. In some embodiments, the staggered arrangement of suction cups improves the ability of the apparatus to grab a piece of lumber that has cracks or other defects, or grab a piece of lumber that is crooked or askew on the pile of lumber from which it is to be picked. In some embodiments, one or more of the staggered rows is separately operable such that one end of the separately operable staggered rows is operable to grab one short piece of lumber and the opposite end and/or the middle of the same row is operable to grab another short piece of lumber.

Some embodiments of the apparatus further include a first venturi, wherein the controller operates the first plurality of air valves to apply compressed air through the first venturi associated with at least a first one of the first plurality of suction cups in order to reduce air pressure within the first one of the plurality of suction cups.

Some embodiments of the apparatus further include a sensor that senses a force between the first one of the first plurality of suction cups and the first piece of lumber, wherein the controller, based on the sensed force being smaller than a predetermined amount, ceases to apply compressed air through the first venturi. In some such embodiments of the apparatus, the controller increases air pressure in the plurality of the first plurality of suction cups to release the first piece of lumber by closing one of the plurality of air valves that applies compressed air through the first venturi. In some such embodiments of the apparatus, the controller increases air pressure in the plurality of the first plurality of suction cups to release the first piece of lumber by opening at least one of the plurality of air valves to supply compressed air into at least one of the first plurality of suction cups.

In some embodiments of the apparatus, the lumber pickup arm further includes a second plurality of selectively air-pressure-activatable suction cups arranged in a staggered configuration, and the apparatus further includes a second venturi and second plurality of air valves, wherein the controller operates the second plurality of air valves to apply compressed air through the second venturi associated with at least a first one of the second plurality of suction cups in order to reduce air pressure within the first one of the second plurality of suction cups.

Some embodiments of the apparatus further include a lumber flipper; a saw unit; and a lumber-analysis unit operably coupled to the lumber picker, wherein the lumber-analysis unit is configured to analyze defects in the first piece of lumber and generate a lumber-defect result based on the analyzed defects, and wherein the gantry structure, the raise/lower actuator, and the lumber pickup arm are configured to move the first piece of lumber from the lumber pile to one of a plurality of destinations that includes the lumber flipper and the saw unit based on the lumber-defect result.

In some embodiments of the apparatus, the lumber-analysis unit is further configured to determine a plurality of dimensions of the first piece of lumber.

In some embodiments of the apparatus, the lumber-analysis unit is configured to analyze crook defects and to determine whether a crown of a board has a crook defect.

In some embodiments of the apparatus, the lumber-analysis unit is configured to analyze twist defects, the lumber-analysis unit is configured to analyze bow defects, the lumber-analysis unit is configured to analyze knot defects, and/or the lumber-analysis unit is configured to analyze wane defects.

Some embodiments of the apparatus further include a plurality of vertically spaced-apart lumber bunks, wherein the lumber pickup arm and gantry structure are operatively coupled to pick a selected piece of lumber from a selected one of the plurality of vertically spaced-apart lumber bunks.

Some embodiments of the apparatus further include a plurality of sets of lumber bunks, wherein each one of the plurality of sets includes a plurality of vertically spaced-apart lumber bunks, and wherein the lumber picker and gantry structure are operatively coupled to pick a selected piece of lumber from a selected one of the plurality of vertically spaced-apart lumber bunks of a selected one of the plurality of sets.

In some embodiments of the apparatus, if the lumber-defect result is acceptable, then the lumber picker is configured to pick up the first piece of lumber from the lumber pile and deliver the first piece of lumber to a saw without reorienting the first piece of lumber.

Some embodiments of the apparatus further include a lumber flipper configured to reorient lumber, wherein if the lumber-defect result is unacceptable, then the lumber picker is configured to pick up the first piece of lumber from the lumber pile and deliver the first piece of lumber to the flipper.

In some embodiments of the apparatus, if the lumber-defect result is unacceptable, then the lumber picker is configured to pick up the first piece of lumber from the lumber pile and deliver the first piece of lumber to a discard pile of lumber.

In some embodiments of the apparatus, the lumber picker includes a plurality of suction cups configured to grasp the first piece of lumber such that the first piece of lumber can be lifted off of the lumber pile and transported.

In some embodiments of the apparatus, the lumber-analysis unit includes one or more optical sensors configured to optically scan the first piece of lumber in order to analyze defects in the first piece of lumber.

In some embodiments of the apparatus, the lumber-analysis unit includes one or more cameras and a computer processor or controller, wherein the one or more cameras are configured to generate images of the first piece of lumber and electronically transmit the images to the processor, and wherein the processor is configured to compare the images to acceptable lumber images.

In some embodiments of the apparatus, the lumber-analysis unit includes one or more cameras and a processor, wherein the one or more cameras are configured to generate images of the first piece of lumber and electronically transmit the images to the processor, and wherein the processor is configured to store an archive of such images for later analysis prompted by a failure of a product made using the first piece of lumber.

In some embodiments, the present invention provides an automated method for processing lumber including: providing a lumber pickup arm that includes a plurality of selectively air-pressure-activatable suction cups arranged in a staggered configuration; locating a selected piece of lumber to be picked up, wherein the selected piece of lumber has a first surface; lowering the pickup arm so that at least some of the plurality of suction cups are seated on the first surface of the selected piece of lumber; reducing air pressure within the at least some of the plurality of suction cups; raising and moving the pickup arm to move the piece of lumber to a first destination; and increasing air pressure within the at least some of the plurality of suction cups to release the piece of lumber at the first destination.

In some embodiments of the method, the reducing of air pressure within the at least some of the plurality of suction cups further includes applying compressed air through a first venturi associated with at least a first one of the plurality of suction cups.

Some embodiments of the method further include sensing a force between the first one of the plurality of suction cups and the first piece of lumber; and based on the sensed force being smaller than a predetermined amount, ceasing the applying of compressed air through the first venturi. In some embodiments, cups not holding vacuum are deactivated, thus reducing the usage of compressed air by ceasing to attempt to achieve a vacuum within suction cups that are not holding onto the piece of lumber. In some embodiments, the controller uses this information to detect that the piece of lumber is not held or has been dropped, which then causes the controller to attempt to again pick up the piece of lumber or to alert a human operator to come over and remove the troublesome piece of lumber.

In some embodiments of the method, the increasing of air pressure within at least some of the plurality of suction cups further includes ceasing the applying of compressed air through the first venturi.

In some embodiments of the method, the increasing of air pressure within at least some of the plurality of suction cups further includes applying compressed air into at least some of the plurality of suction cups.

Some embodiments of the method further include before the lowering of the pickup arm so that at least some of the plurality of suction cups are seated on the first surface of the selected piece of lumber, initially lowering the pickup arm so that at least some of the plurality of suction cups are near but not seated on the piece of lumber; and blowing debris away using compressed air released either through the suction cups, around the suction cups, or both through and around the suction cups.

Some embodiments of the method further include providing a first plurality of lumber bunks, wherein each one of the first plurality of lumber bunks is vertically displaced relative to at least one other of the first plurality of lumber bunks, and wherein each bunk of the first plurality of lumber bunks is configured to hold a stack of lumber; selecting a first lumber stack from the first plurality of lumber bunks; inspecting a first lumber piece on the first lumber stack and generating an analysis result based on the inspecting; picking up the first lumber piece from the first lumber stack; and transporting the first lumber piece to a processing location that is chosen based on the analysis result, wherein the transporting includes moving the first lumber piece in a direction that parallels a longitudinal axis of the first lumber stack.

In some embodiments of the method, the analysis result identifies the first lumber piece as unacceptable, and the transporting includes moving the first lumber piece to a discard pile.

In some embodiments of the method, the analysis result identifies the first lumber piece as requiring reorientation, and the transporting includes moving the first lumber piece to a lumber flipper configured to reorient the first lumber piece prior to further processing of the first lumber piece.

In some embodiments of the method, the analysis result identifies the first lumber piece as acceptable, and the transporting includes moving the first lumber piece to a saw station.

Some embodiments of the method further include providing a second plurality of lumber bunks, wherein each one of the second plurality of lumber bunks is vertically displaced relative to at least one other of the second plurality of lumber bunks, wherein the second plurality of lumber bunks is horizontally displaced relative to the first plurality of lumber bunks, and wherein the transporting includes moving the first lumber piece along a path that runs in between the first plurality of lumber bunks and the second plurality of lumber bunks.

Some embodiments of the method further include providing a processor operatively coupled to a plurality of user devices, a database, and a plurality of sensors; and eliciting and receiving acceptable-lumber data from at least one of the plurality of user devices, wherein the inspecting includes gathering physical data of the first lumber piece using the plurality of sensors and storing the physical data in the database, and wherein the generating of the analysis result includes comparing the physical data to the acceptable-lumber data using the processor.

In some embodiments, the present invention provides an apparatus for automated processing of lumber, This apparatus includes: a lumber pickup arm that includes a plurality of selectively air-pressure-activatable suction cups arranged in a staggered configuration; means for locating a selected piece of lumber to be picked up, wherein the selected piece of lumber has a first surface; means for lowering the pickup arm so that at least some of the plurality of suction cups are seated on the first surface of the selected piece of lumber; means for reducing air pressure within the at least some of the plurality of suction cups; means for raising and moving the pickup arm to move the piece of lumber to a first destination; and means for releasing the piece of lumber at the first destination.

Some embodiments of the apparatus further include a first plurality of lumber bunks, wherein each one of the first plurality of lumber bunks is vertically displaced relative to at least one other of the first plurality of lumber bunks, and wherein each bunk of the first plurality of lumber bunks is configured to hold a stack of lumber; means for selecting a first lumber stack from the first plurality of lumber bunks; means for inspecting a first lumber piece on the first lumber stack and generating an analysis result based on the inspecting; means for picking up the first lumber piece from the first lumber stack; and means for transporting the first lumber piece to a processing location that is chosen based on the analysis result, wherein the means for transporting moves the first lumber piece in a direction that parallels a longitudinal axis of the first lumber piece.

Some embodiments of the apparatus further include a second plurality of lumber bunks, wherein each one of the second plurality of lumber bunks is vertically displaced relative to at least one other of the second plurality of lumber bunks, wherein the second plurality of lumber bunks is horizontally displaced relative to the first plurality of lumber bunks, and wherein the transporting includes moving the first lumber piece along a path that runs along the first plurality of lumber bunks and the second plurality of lumber bunks.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus for manipulating a first piece of lumber, wherein the first piece of lumber is one of a plurality of lumber pieces on a lumber pile, and wherein the first piece of lumber has a first surface, the apparatus comprising:
   a gantry structure that includes a raise/lower actuator;
   a lumber pickup arm operatively coupled to the raise/lower actuator of the gantry structure, wherein the lumber pickup arm includes a first plurality of selectively air-pressure-activatable suction cups arranged in a staggered configuration;
   a first plurality of air valves operably connected to the first plurality of suction cups;
   an optical location device configured to generate location parameters for where the first piece of lumber is to be picked up;
   a controller operably connected to the first plurality of air valves and configured to control the raise/lower actuator to lower the lumber pickup arm based on the location parameters of where the first piece of lumber is to be picked up so that a first sub-plurality of the first plurality of suction cups seat on the first surface of the first piece of lumber, and to operate the first plurality of air valves so as to reduce air pressure in the first sub-plurality of the first plurality of suction cups to grab the first piece of lumber, wherein the controller later activates at least one of the first plurality of air valves to supply compressed air into at least one of the first sub-plurality of the first plurality of suction cups to increase air pressure in the at least one of the first sub-plurality of the first plurality of suction cups to release the first piece of lumber; and
   a lumber-analysis unit operably coupled to the lumber pickup arm, wherein the lumber-analysis unit is configured to perform a defect analysis on the first piece of lumber and generate a lumber-defect result based on the defect analysis, wherein the defect analysis includes a comparison of physical geometric data of the first piece of lumber to acceptable lumber parameters, and wherein the gantry structure, the raise/lower actuator, and the lumber pickup arm are configured to move the first piece of lumber from the lumber pile to one of a plurality of destinations based on the lumber-defect result.

2. The apparatus of claim 1, further comprising: a first venturi, wherein the controller operates the first plurality of air valves to apply compressed air through the first venturi associated with at least a first one of the first plurality of suction cups in order to reduce air pressure within the first one of the first plurality of suction cups.

3. The apparatus of claim 2, further comprising: a sensor that senses a force between the first one of the first plurality of suction cups and the first piece of lumber, wherein the controller, based on the sensed force being smaller than a predetermined amount, ceases to apply compressed air through the first venturi.

4. The apparatus of claim 2, wherein the controller also increases air pressure in the first sub-plurality of the first plurality of suction cups to release the first piece of lumber by closing one of the first plurality of air valves that applies compressed air through the first venturi.

5. The apparatus of claim 2, wherein the lumber pickup arm further includes a second plurality of selectively air-pressure-activatable suction cups arranged in a staggered configuration, and wherein the apparatus further includes a second venturi and second plurality of air valves, wherein the controller operates the second plurality of air valves to apply compressed air through the second venturi associated with at least a first one of the second plurality of suction cups in order to reduce air pressure within the first one of the second plurality of suction cups.

6. The apparatus of claim 2, further comprising:
   a lumber flipper; and
   a saw unit, wherein the plurality of destinations includes the lumber flipper and the saw unit.

7. The apparatus of claim 1, further comprising a plurality of vertically spaced-apart lumber bunks, wherein the lumber pickup arm and gantry structure are operatively coupled to pick a selected piece of lumber from a selected one of the plurality of vertically spaced-apart lumber bunks.

8. The apparatus of claim 1, further comprising a plurality of sets of lumber bunks, wherein each one of the plurality of sets includes a plurality of vertically spaced-apart lumber bunks, wherein the lumber pickup arm and gantry structure are operatively coupled to pick a selected piece of lumber from a selected one of the plurality of vertically spaced-apart lumber bunks of a selected one of the plurality of sets.

9. The apparatus of claim 1, further comprising:
   a sensor that senses a force between a first one of the first plurality of suction cups and the first piece of lumber, wherein the controller, based on the sensed force being smaller than a predetermined amount, further reduces air pressure within the first one of the first plurality of suction cups.

10. The apparatus of claim 1, wherein the controller also increases air pressure in the at least one of the first sub-plurality of the first plurality of suction cups to release the first piece of lumber by closing one of the first plurality of air valves.

11. The apparatus of claim 1, wherein the controller increases air pressure in the at least one of the first sub-plurality of the first plurality of suction cups to release the first piece of lumber by opening the at least one of the first plurality of air valves.

12. The apparatus of claim 1, wherein the lumber pickup arm further includes a second plurality of selectively air-pressure-activatable suction cups arranged in a staggered configuration, and wherein the apparatus further includes a second plurality of air valves, wherein the controller operates the second plurality of air valves to reduce air pressure within at least a first one of the second plurality of suction cups.

13. The apparatus of claim 1, further comprising:
   a lumber flipper; and
   a saw unit, wherein the plurality of destinations includes the lumber flipper and the saw unit.

14. The apparatus of claim 1, wherein the apparatus is configured to access a first plurality of lumber bunks, wherein each one of the first plurality of lumber bunks is vertically displaced relative to at least one other of the first plurality of lumber bunks, and wherein a first lumber bunk of the first plurality of lumber bunks is configured to hold the lumber pile that includes the first piece of lumber, and a second plurality of lumber bunks, wherein each one of the second plurality of lumber bunks is vertically displaced relative to at least one other of the second plurality of lumber bunks, and wherein the second plurality of lumber bunks is horizontally displaced relative to the first plurality of lumber bunks; and wherein the gantry structure, the raise/lower actuator, and the lumber pickup arm are further configured to move the first piece of lumber from the lumber pile in a direction that parallels a longitudinal axis of the lumber pile and along a path that runs in between the first plurality of lumber bunks and the second plurality of lumber bunks.

15. The apparatus of claim 1, wherein the lumber-analysis unit includes:
   a plurality of user devices,
   a database,
   a plurality of sensors, and
   a processor, wherein the processor is operatively coupled to the plurality of user devices, the database, and the plurality of sensors,
   wherein at least one of the plurality of user devices provides the acceptable lumber parameters, wherein the plurality of sensors is configured to gather the physical geometric data of the first piece of lumber, wherein the database is configured to store the physical geometric data, and wherein the processor is configured to perform the comparison of the physical geometric data to the acceptable lumber parameters.

16. The apparatus of claim 1, wherein the controller is further configured to operate the first plurality of air valves such that debris on the first piece of lumber is blown away.

17. The apparatus of claim 1, wherein the staggered configuration of the first plurality of selectively air-pressure-activatable suction cups includes a first suction cup, a second suction cup, and a third suction cup arranged sequentially in a row having a centerline, wherein the first suction cup and the third suction cup are on a first side of the centerline, wherein the second suction cup is on a second, opposite, side of the centerline, and wherein the second suction cup is the only suction cup between the first suction cup and the third suction cup in the row.

* * * * *